United States Patent [19]
Albright

[11] Patent Number: 5,288,720
[45] Date of Patent: Feb. 22, 1994

[54] ANGIOTENSIN II RECEPTOR BLOCKING 2,3,6 SUBSTITUTED QUINAZOLINONES

[75] Inventor: Jay D. Albright, Nanuet, N.Y.

[73] Assignee: American Cyanamid Company, Wayne, N.J.

[21] Appl. No.: 52,940

[22] Filed: Apr. 23, 1993

[51] Int. Cl.$^5$ ............... C07D 239/91; C07D 403/10; A61K 31/505; A01N 43/54
[52] U.S. Cl. .................... 514/259; 544/284; 544/287; 514/260
[58] Field of Search .............. 544/284, 287; 514/259, 514/260

[56] References Cited

U.S. PATENT DOCUMENTS

| 5,202,322 | 4/1993 | Allen et al. | 514/228.2 |
| 5,238,942 | 8/1993 | Chakravarty et al. | 514/259 |
| 5,240,928 | 8/1993 | Allen et al. | 514/259 |

FOREIGN PATENT DOCUMENTS

| 407342 | 6/1990 | European Pat. Off. |
| 411766 | 6/1990 | European Pat. Off. |
| 445811 | 3/1991 | European Pat. Off. |
| 481448 | 10/1991 | European Pat. Off. |
| 512870 | 11/1992 | European Pat. Off. |

Primary Examiner—Mukund J. Shah
Assistant Examiner—Matthew V. Grumbling
Attorney, Agent, or Firm—Thomas S. Szatkowski

[57] ABSTRACT

Novel 2, 3, 6 substituted quinazolinones of the formula:

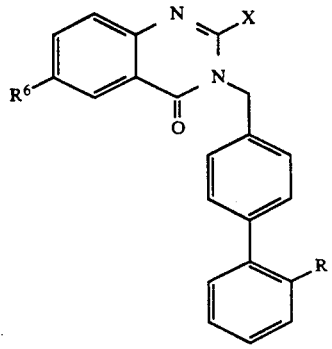

Formula I wherein R, $R^6$ and X are described in the specification are disclosed. The compounds which have activity as angiotensin II (AII) antagonists.

38 Claims, No Drawings

ANGIOTENSIN II RECEPTOR BLOCKING 2,3,6 SUBSTITUTED QUINAZOLINONES

BACKGROUND OF THE INVENTION

1. Field of the Invention

This invention relates to certain novel 2, 3, 6 substituted quinazolinone compounds which have demonstrated activity as angiotensin II (AII) antagonists and are therefore useful in alleviating angiotensin induced hypertension and for treating congestive heart failure.

SUMMARY OF THE INVENTION

According to the present invention, there are provided novel compounds of Formula I which have angiotensin II-antagonizing properties and are useful as antihypertensives:

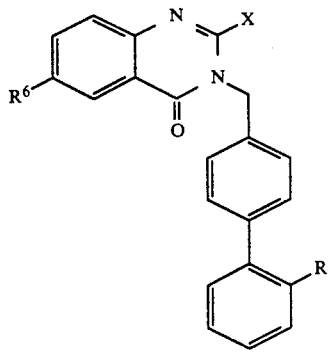

Formula I wherein:
R is

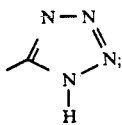

X is straight or branched alkyl of 3 to 5 carbon atoms;
$R^6$ is

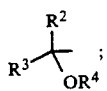

$R^2$ is H, or straight chain lower alkyl of 1 to 4 carbon atoms;
$R^3$ is

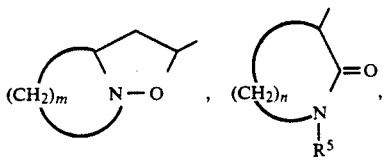

-continued

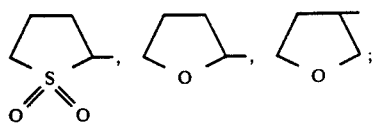

n is 2, 3 or 4;
m is 3 or 4:
$R^4$ is H, or straight chain lower alkyl of 1 to 4 carbon atoms;
$R^5$ is straight chain lower alkyl of 1 to 4 carbon atoms; and the pharmaceutically acceptable salts thereof.

The present invention also provides novel intermediate compounds, methods for making the novel 2, 3, 6 substituted quinazolinone angiotensin II antagonizing compounds, methods for making the novel intermediates, methods of using the novel quinazolinone angiotensin II antagonizing compounds to treat hypertension, congestive heart failure and to antagonize the effects of angiotensin II.

DETAILED DESCRIPTION OF THE INVENTION

The novel compounds of the present invention are prepared according to the following reaction schemes.

Referring to Scheme I, the corresponding anthranilic acids 2 where is $R^{10}$ is I, Br or $CH_3$, are heated to reflux in alkyl acid anhydride 3 wherein X is alkyl of 3 to 5 carbon atoms to provide the 4H-3,1-benzoxazin-4-ones 4 which are isolated by concentrating the reaction mixtures and used without further purification. When the 4H-3,1-benzoxazin-4-ones 4 are refluxed in ethyl alcohol containing ammonia, or ammonium hydroxide solution, the quinazolinone intermediates 5 are obtained.

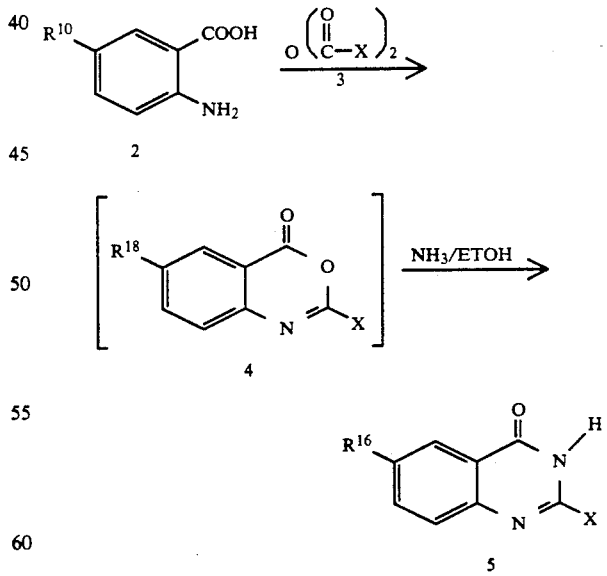

Scheme I

The quinazolinone intermediates 5 are modified according to the following reaction schemes to obtain the novel quinazolinone angiotensin II antagonizing compounds of the present invention.

In Scheme II, 6-methyl-2-(lower alkyl)-4(1H)-quinazolinone 6, as prepared by Scheme I, is brominated with N-bromosuccinimide to give the bromomethyl compound 7. Hydrolysis of the bromide with aqueous potassium carbonate in dimethylsulfoxide yields the primary alcohol 8. The alcohol 8 is oxidized with pyridinium dichromate in N,N-dimethylformamide to afford aldehyde 9. The aldehyde 9 is reacted with a variety of Grignard Reagents R²MgBr or lithium reagents R²Li in tetrahydrofuran where R² is as defined hereinabove, except that for this reaction scheme R² cannot be H, to give the desired secondary alcohol 10. Alcohol 10 is oxidized with pyridinium dichromate in N,N-dimethylformamide to afford 6-(1-oxo-(lower alkyl)-2-(lower alkyl)-4(1H)-quinazolinone 11.

-continued
Scheme III

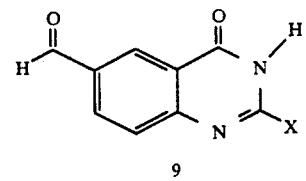

In an alternative route to 6-(1-oxo-(lower alkyl)-2-

Scheme II

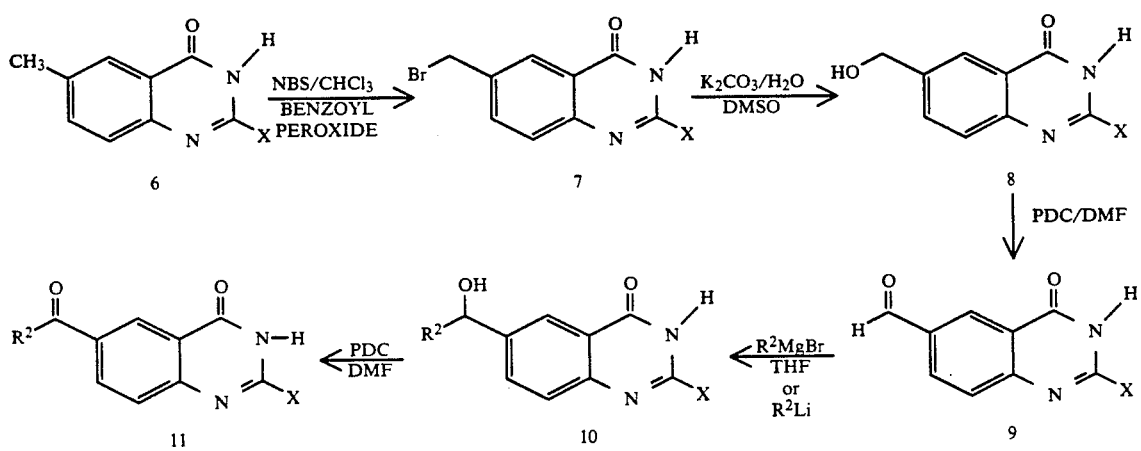

In an alternate route to 9, as shown in Scheme III, 2-alkyl substituted-6-iodo-4 (1H)-quinazolinone 12 prepared by Scheme I is reacted via a palladium catalyzed carbonylation to give aldehyde 9.

Scheme III

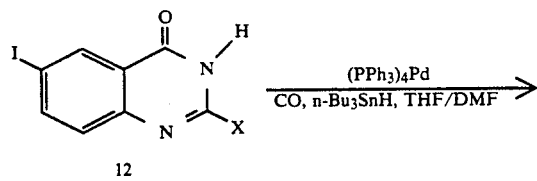

(lower alkyl)-4(1H)-quinazolinone, 11, shown in Scheme IV, the palladium (II) catalyzed coupling of (trimethylsilyl)acetylene with 2-alkylsubstituted-6-iodo-4(1H)-quinazolinone 12 yields the acetylenic quinazolinone 13. Desilylation of the acetylene with sodium hydroxide in water-methanol gives the terminal acetylene 14. Hydration of acetylene 14 with catalytic mercuric sulfate-sulfuric acid in acetic acid affords 6-acetyl-2-(lower alkyl)-4(1H)-quinazolinone. The palladium (II) catalyzed coupling of substituted acetylenes where R² is as defined hereinabove except that for this reaction scheme R² cannot be H with 2-alkyl-substituted-6-iodo-4(1H)-quinazolinone 12 yields the acetylenic quinazolinone 16. Hydration of 16 with catalytic mercuric sulfate-sulfuric acid in acetic acid gives 11.

Scheme IV

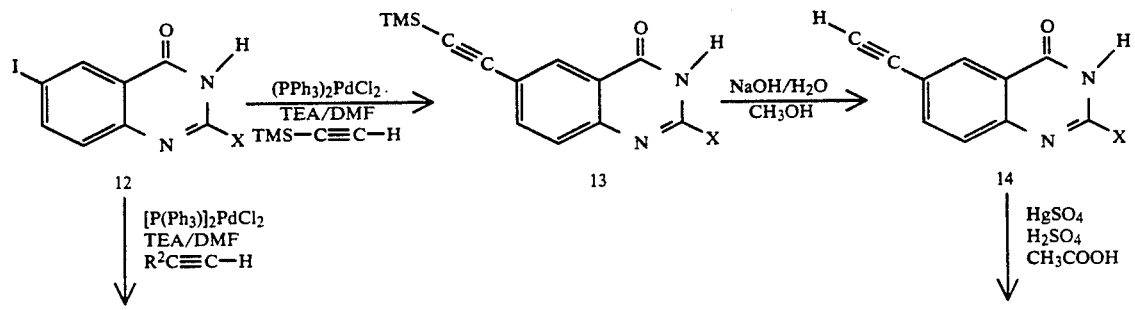

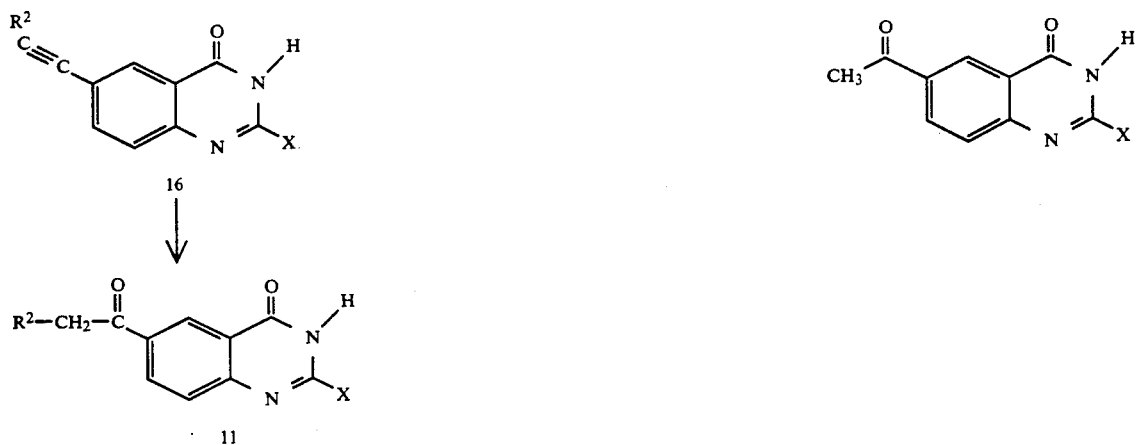

As shown in Scheme V, quinazolinone intermediate 9 where X is hereinbefore defined is reacted with tetramethylene sulfone 19 in the presence of butyl lithium at −78° C. to give alcohol 20. The quinazolinone 11 where $R^2$ is a straight chain lower alkyl of 1 to 4 carbon atoms is reacted with the anion of tetramethylene sulfone prepared from 19, n-butyllithium and $CeCl_3$ to give alcohol 21.

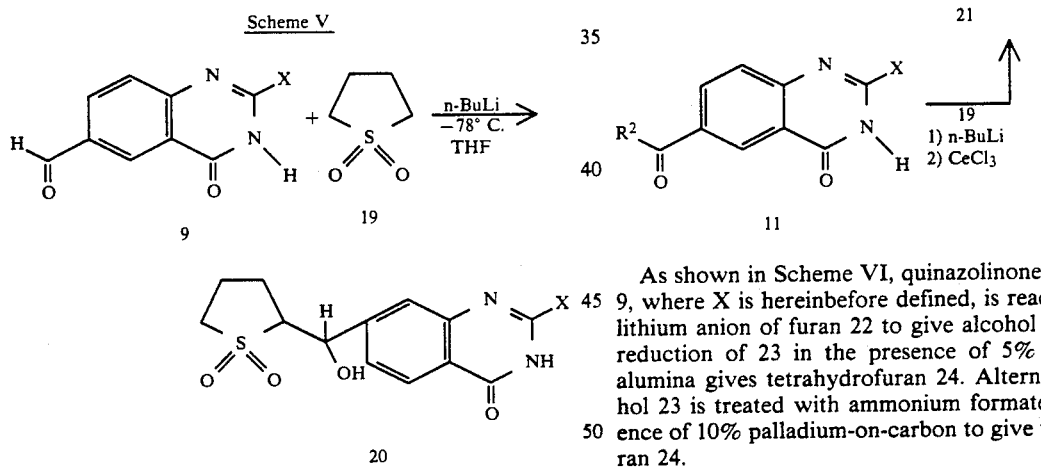

As shown in Scheme VI, quinazolinone intermediate 9, where X is hereinbefore defined, is reacted with the lithium anion of furan 22 to give alcohol 23. Catalytic reduction of 23 in the presence of 5% rhodium-on-alumina gives tetrahydrofuran 24. Alternatively, alcohol 23 is treated with ammonium formate in the presence of 10% palladium-on-carbon to give tetrahydrofuran 24.

Reaction of intermediate 11 where for this reaction scheme $R^2$ is a straight chain lower alkyl ($C_1$–$C_4$) group with the anion of Scheme VI

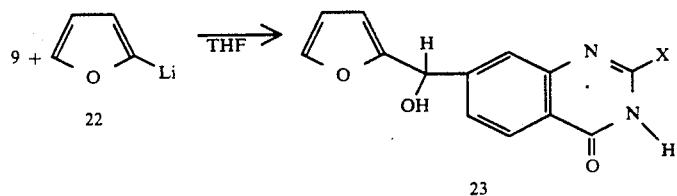

Scheme VI

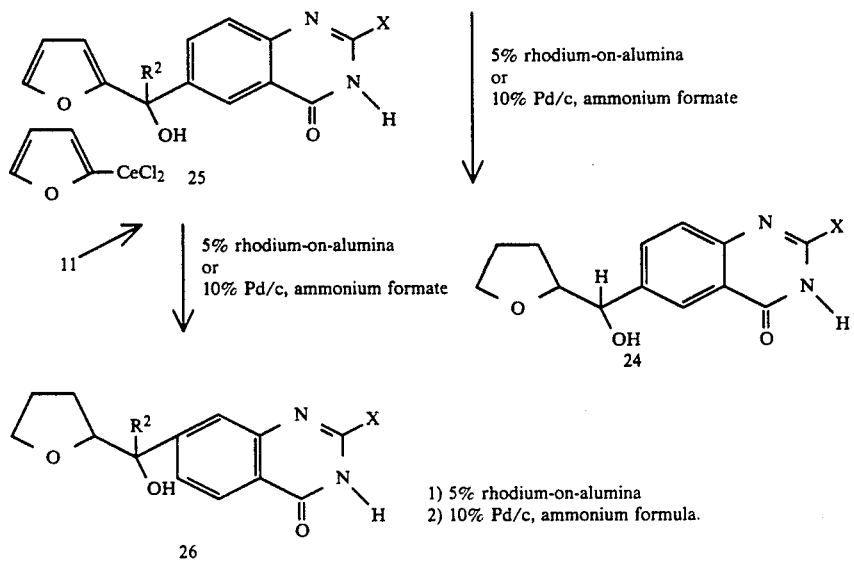

furan prepared from furan, n-butyl lithium and CeCl₃ gives alcohol 25. Catalytic reduction of 25 in the presence of 5% rhodium-on-alumina or treatment of 25 with ammonium formate in the presence of 10% palladium-on-carbon gives tetrahydrofuran 26.

As shown in Scheme VII, lithium bis(trimethylsilyl)amide is reacted with pyrrolidinone 27 where $R^5$ is hereinbefore defined, at −78° C. in tetrahydrofuran to afford the lithium salt 28 which is reacted with quinazolinone 9, where X is hereinbefore defined, to afford alcohol 29. Reaction of lithium anion 28 with CeCl₃ and reaction of the resulting anion 30 with 11

Scheme VII

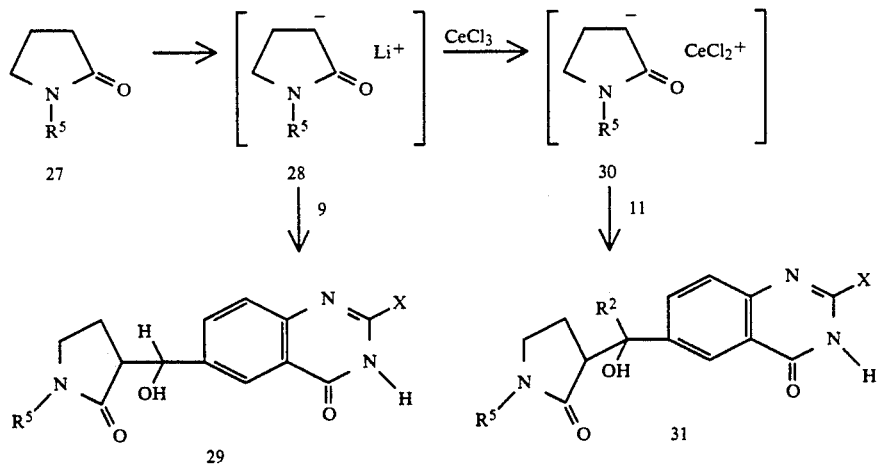

where $R^2$ and X are hereinbefore defined gives alcohol 31.

As shown in Scheme VIII, reaction of lithium bis(trimethylsilyl)amide with piperidone 32, where $R^5$ is hereinbefore defined at −78° C. in tetrahydrofuran gives lithium salt 33 which is reacted with quinazolinone 9, where X is hereinbefore defined to give alcohol 34. Reaction of the lithium salt 33 with CeCl₃ and reaction of the resulting anion 35 with 11 where $R^2$ is as defined hereinbefore gives the intermediate alcohol 36.

Scheme VIII

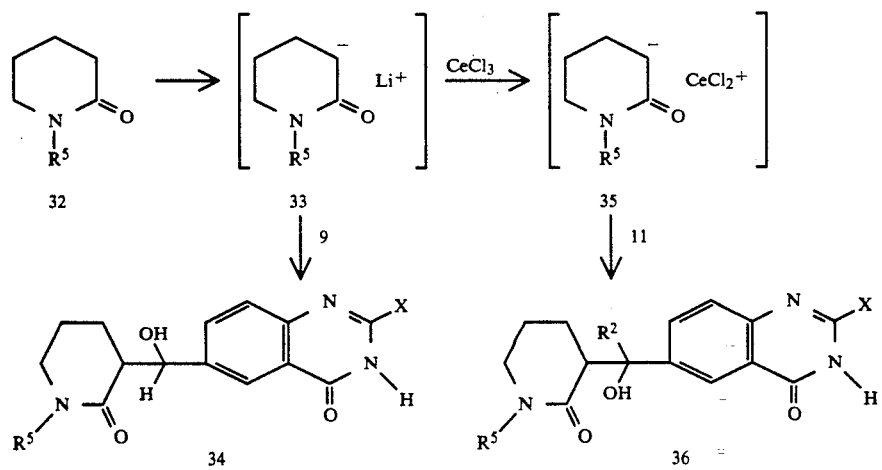

As described in EP 0 497 150, biphenyl 38 is attached to quinazolinone intermediates 20, 21, 24, 26, 29, 31, 34, or 36, by initially alkylating the quinazolinone with a para-substituted benzyl bromide and subsequently attaching a second phenyl moiety containing a trityl protected tetrazole or a cyano via transition metal catalyzed coupling at the para position of the first phenyl ring. Alternatively, the coupling of quinazolinone intermediates 20, 21, 24. 26, 29, 31. 34, or 36, with biphenyl 38 where is a trityl protected tetrazole prepared by the methods of N. B. Mantlo et al, *J. Med. Chem.* 34 2919-2922 (1991) or cyano prepared by the methods outlined in D. J. Carini, *J. Med. Chem.* 34, 2525-2547 (1991) is illustrated in Scheme IX and gives coupled product 39 by dissolving the particular intermediate and 38 in acetone or another suitable solvent such as N,N-dimethylformamide, N,N-dimethylacetamide, N-methylpyrrolidinone, methanol, ethanol, t-butanol, tetrahydrofuran, dioane or dimethylsulfoxide, in the presence of excess potassium carbonate or another suitable base such as sodium carbonate, cesium carbonate, sodium hydride, potassium hydride, sodium methoxide, sodium ethoxide, lithium methoxide, sodium t-butoxide, potassium t-butoxide, lithium diisopropylamide (LDA) or lithium hexamethyldisilazide for 2-48 hours, at 20°-60° C. The obtained alkylated quinazolinone 39 may be purified by chromatography or used as is in further transformations and/or deprotection.

Reaction of 39 where $R^{18}$ is cyano with sodium azide in the presence of tri-n-butyltin chloride in refluxing xylene affords the desired tetrazole 40. Contemplated equivalents o tri-n-butyltin chloride include tri-(lower-alkyl $C_1$-$C_4$) tin chlorides and bromides. Contemplated equivalents to sodium azide include potassium azide, lithium azide and cesium azide. Hydrolysis of 39 where $R^{18}$ is a trityl protected tetrazole with methanol-tetrahydrofuran at room temperature to reflux or a catalytic amount of hydrochloric acid or other suitable acid such as sulfuric, trifluoroacetic or hydrogen chloride for 10 minutes to 24 hours at room temperature affords the free tetrazole 40.

Scheme IX

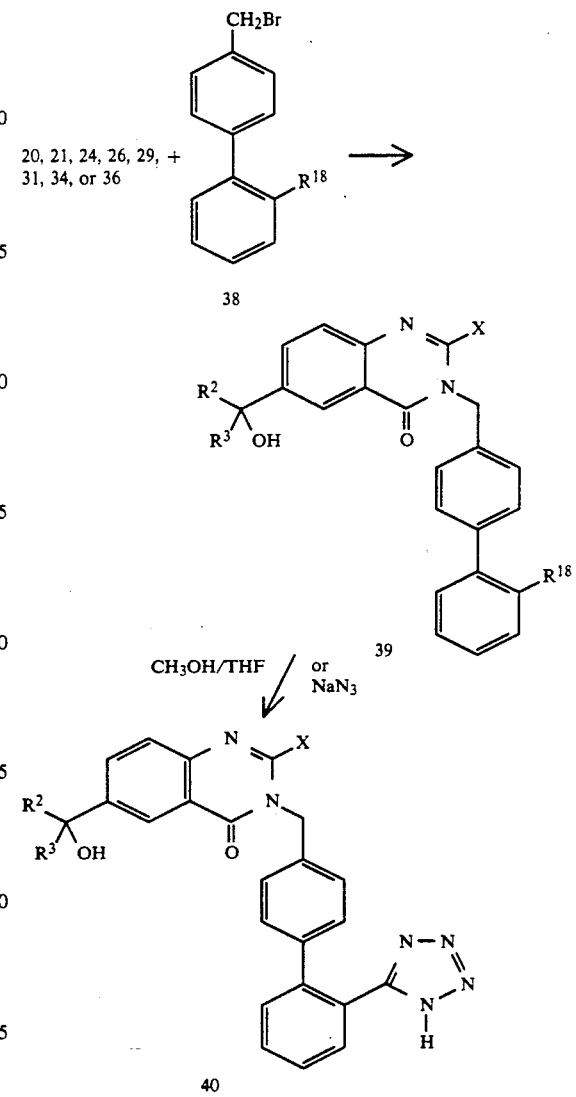

As shown in Scheme alkylated quinazolinone 39, where $R^2$, $R^3$, $R^{18}$ and X are hereinbefore defined is alkylated with $R^4$ I, where for this reaction scheme $R^4$ is straight chain lower alkyl ($C_1$-$C_4$) group to give ether 41. Reaction of 41 where $R^{18}$ is cyano with sodium azide in the presence of tri-n-butyltin chloride in refluxing xylene affords the desired tetrazole 42. Contemplated equivalents to tri-n-butyltin chloride include tri-(lower alkyl $C_1$-$C_4$) tin chloride and bromides. Contemplated equivalents to sodium azide include potassium azide, lithium azide and cesium azide. Hydrolysis of 41 where $R^{18}$ is a trityl protected tetrazole with methanol-tetrahydrofuran at room temperature to reflux or a catalytic amount of hydrochloric acid or other suitable acid such as sulfuric, trifluoroacetic or hydrogen chloride for 10 minutes to 24 hours at room temperature affords the free tetrazole 42.

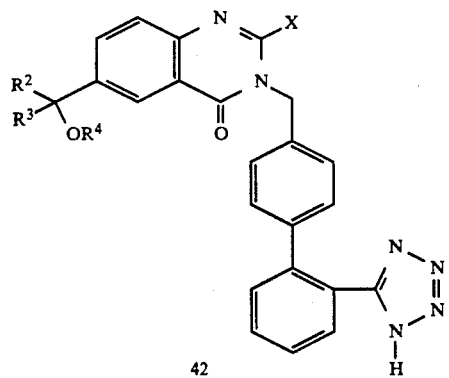

The coupling of quinazolinone intermediate 25 where $R^2$ and X are hereinbefore defined with biphenyl 38 where is hereinbefore defined, under the conditions outlined of Scheme IX, is shown in Scheme XI to give 44. Catalytic reduction of 44 in the presence of 5% rhodium-on-alumina gives tetrahydrofuran 45. Alternatively, alcohol 44 is treated with ammonium formate in the presence of 10% palladium-on-carbon to give tetrahydrofuran 45. Alkylation of alcohol 45 with $R^4$ I, where for this reaction scheme $R^4$ is lower alkyl $C_1$-$C_4$ in the presence of base gives ether 46. Reaction of 46 where $R^{18}$ is cyano with sodium azide in the presence of tri-n-butyltin chloride in refluxing xylene affords the desired tetrazole 47. Contemplated equivalents to tri-n-butyltin chloride include tri-(lower alkyl $C_1$-$C_4$)tin chlorides and bromides. Contemplated equivalents to sodium azide include potassium azide, lithium aside and cesium azide. Hydrolysis of 46 where $R^{18}$ is a trityl protected tetrazole with methanol-tetrahydrofuran at room temperature to reflux or a catalytic amount of hydrochloric acid or other suitable acid such as sulfuric, trifluoroacetic or hydrogen chloride for 10 minutes to 24 hours at room temperature affords the free tetrazole 47.

Scheme X

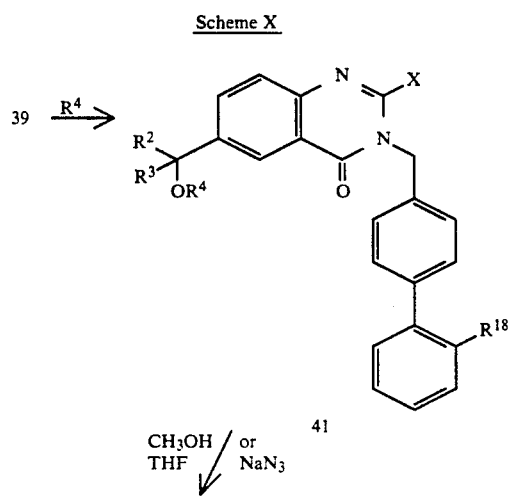

Scheme XI

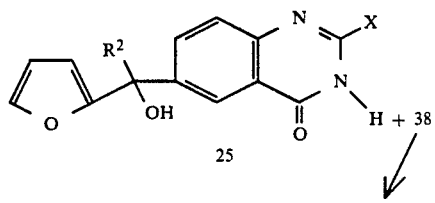

-continued
Scheme XI

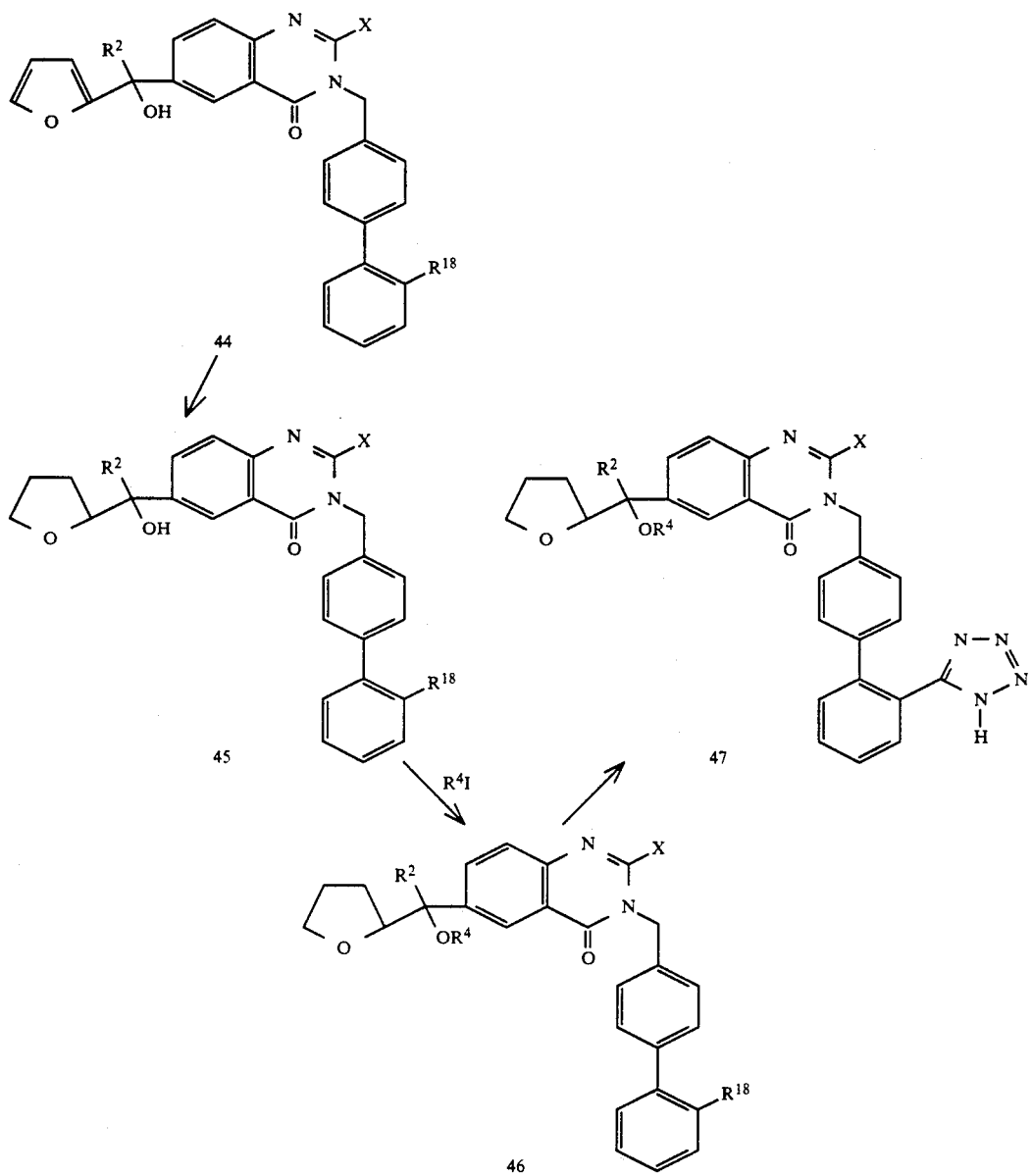

Referring to Scheme XII, Quinazolinone intermediate 48 containing an olefinic substituent is prepared by reacting compounds of formulae 9 or 11 with vinyllithium or vinyl magnesium bromide using methods of H. Neumann and D. Seebach, *Tetrahedron Letters*, 4839 (1976) and G. Kobrich and H. Trapp, *Ber.*, 99, 680 (1966). The preparation of cyclic nitrone intermediates 49 is described by S-I Murahashi and T. Shrota in *Tetrahedron Letters*, 28, 2383 (1987) and by S-I Murahashi, H. Anitsui, T. Shrota, T. Tsuda and S. Watanabe in *J. Org. Chem;* 55, 1736 (1990) and references therein. Cyclic nitrones 49 are useful 1,3-dipoles and undergo cycloaddition reactions depicted in Scheme XII.

As shown in Scheme XII, quinazolinone intermediate 48, where X and $R^2$ are hereinbefore defined, is reacted with cyclic nitrone intermediate 49 where m is 3 or 4 to give the cycloaddition derivatives 50. Under conditions previously described in Scheme IX alkylation of 50 with bromoderivative 38 gives the alkylated quinazolinone 51. Reaction of 51 where $R^{18}$ is cyano with sodium azide in the presence of tri-n-butyltin chloride in refluxing xylene affords the desired tetrazole 52. Contemplated equivalents to tri-n-butyltin chloride include tri-(lower alkyl $C_1$-$C_4$) tin chlorides and bromides Contemplated equivalents to sodium azide include potassium azide, lithium azide and cesium azide. Hydrolysis of 51 where $R^{18}$ is a trityl protected tetrazole with methanol-tetrahydrofuran at room temperature to reflux or a catalytic amount of hydrochloric acid or other suitable and such as sulfuric, trifluoroacetic or hydrogen chloride for 10 minutes to 24 hours at room temperature affords the free tetrazole 52.

Reaction of 51 where $R^2$, $R^{18}$, X and m are hereinbefore defined, with $R^4I$, where $R^4$ is hereinbefore defined, except that for this reaction scheme $R^4$ cannot be H, gives alkylated product 53. Reaction of 53 where $R^{18}$ is cyano with sodium azide in the presence of tri-n-butyltin chloride in refluxing xylene affords the desired tetrazole 54. Contemplated equivalents to tri-n-butyltin chloride include tri(lower alkyl $C_1$-$C_4$) tin chlorides and bromides. Contemplated equivalents to sodium azide include potassium azide, lithium azide and cesium azide. Hydrolysis of 53 where $R^{18}$ is a trityl protected tetrazole with methanol-tetrahydrofuran at room temperature to reflux or a catalytic amount of hydrochloric acid or other suitable acid such as sulfuric, trifluoroacetic or hydrogen chloride for 10 minutes to 24 hours at room temperature affords the free tetrazole 54.

Alternatively, as shown in Scheme XIII, the quinazolinone intermediate 48, where X and $R^2$ are hereinbefore defined, is coupled to biphenyl 38, where $R^{18}$ is hereinbefore defined, using the conditions of Scheme IX to give intermediate 55. Reaction of 55 with cyclic nitrone intermediate 49 where m is 3 or 4 gives cyclo addition derivatives 51.

Reaction of 51 where $R^{18}$ is cyanao with sodium azide in the presence of tri-n-butyltin chloride in refluxing xylene affords the desired tetrazole 52. Contemplated equivalents to tri-n-butyltin chloride include tri-(lower alkyl $C_1$-$C_4$) tin chlorides and bromides. Contemplated equivalents to sodium azide include potassium azide, lithium azide and cesium azide. Hydrolysis of 51 where $R^{18}$ is a trityl protected tetrazole with methanol-tetrahydrofuran at room temperature to reflux or a catalytic amount of hydrochloric acid or other suitable acid such as sulfuric, trifluoroacetic or hydrogen chloride for 10 minutes to 24 hours at room temperature affords the free tetrazole 52.

Reaction of 51 where $R^2$, $R^{18}$, X and m are hereinbefore defined, with $R^4I$, where $R^4$ is hereinbefore defined, except that for this reaction scheme $R^4$ cannot be H, gives alkylated product 53. Reaction of 53 where $R^{18}$ is cyano with sodium azide in the presence of tri-n-butyltin chloride in refluxing xylene affords the desired tetrazole 54. Contemplated equivalents to tri-n-butyltin chloride include tri-(lower alkyl $C_1$-$C_4$) tin chlorides and bromides. Contemplated equivalents to sodium azide include potassium azide, lithium azide and cesium azide. Hydrolysis of 53 where $R^{18}$ is a trityl protected tetrazole with methanol-tetrahydrofuran at room temperature to reflux or a catalytic amount of hydrochloric acid or other suitable acid such as sulfuric, trifluoroacetic or hydrogen chloride for 10 minutes to 24 hours at room temperature affords the free tetrazole 54.

Scheme XII

-continued
Scheme XII

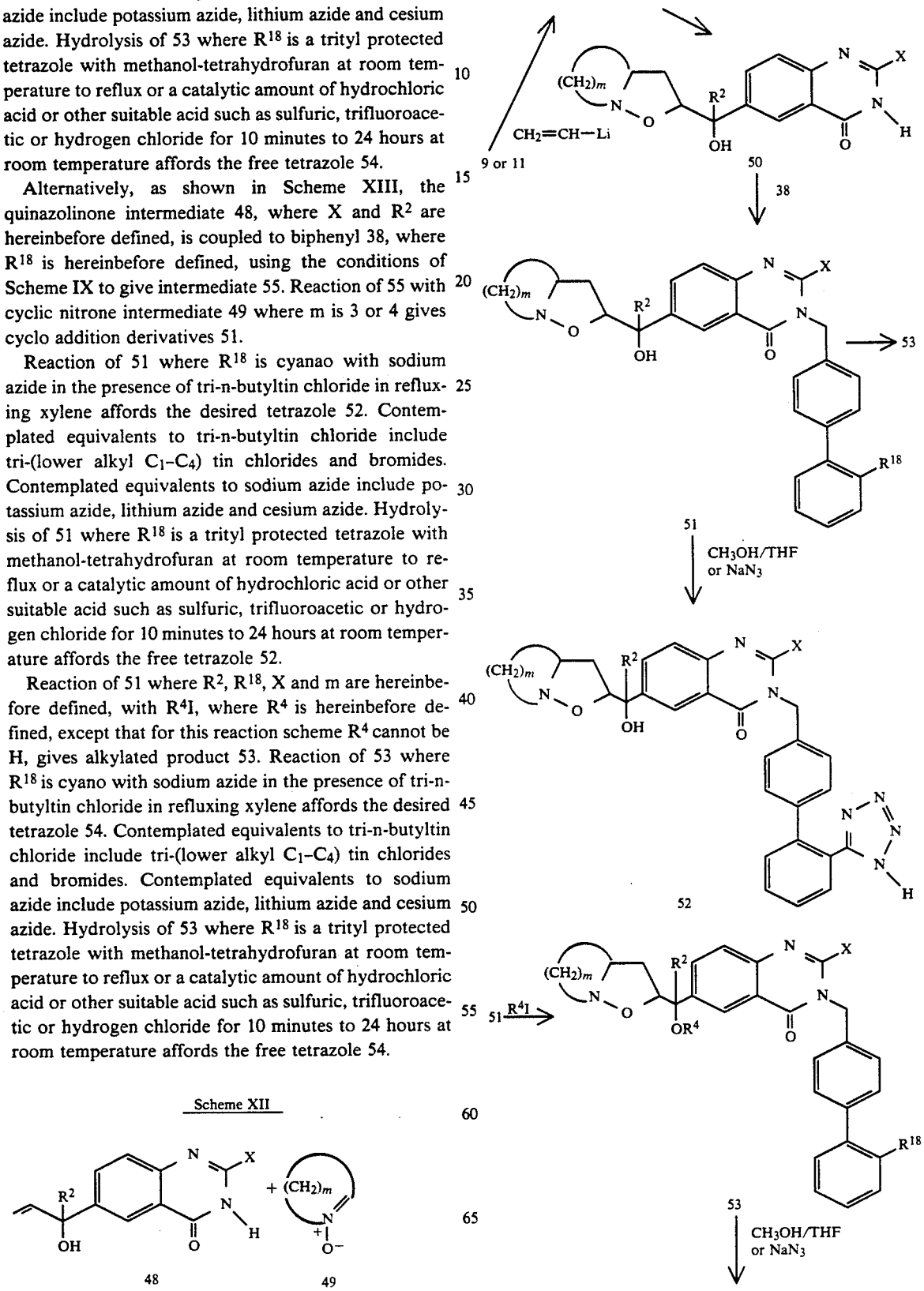

-continued
Scheme XII

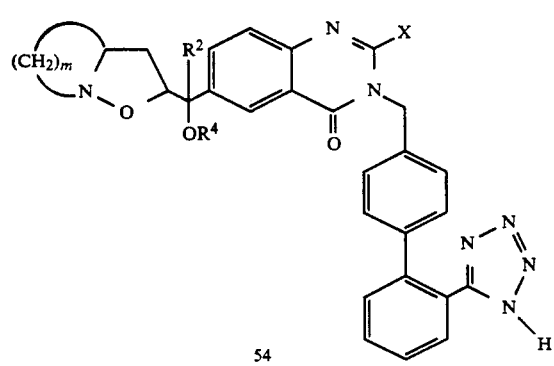

Scheme XIII

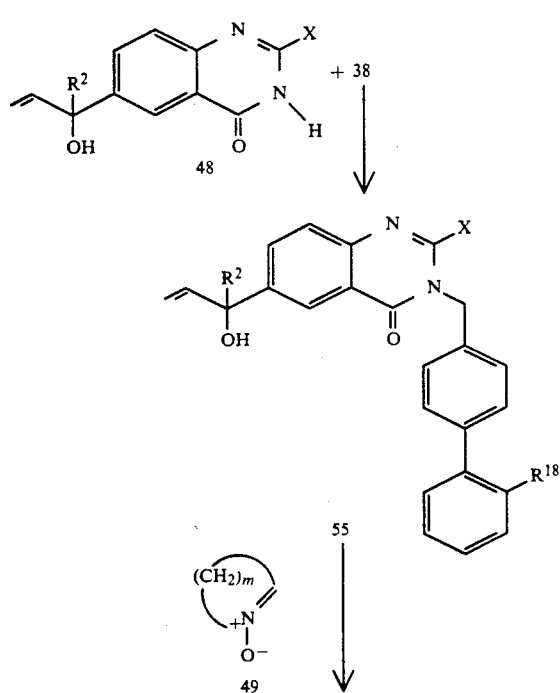

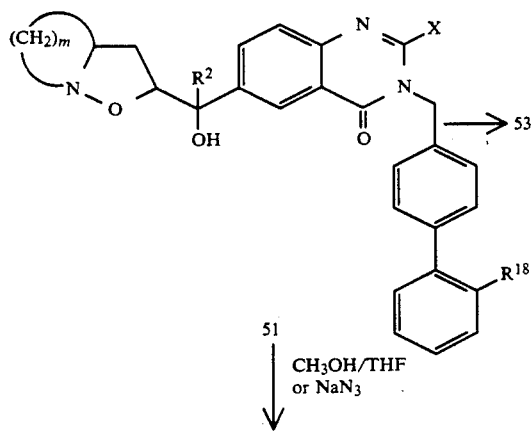

-continued
Scheme XIII

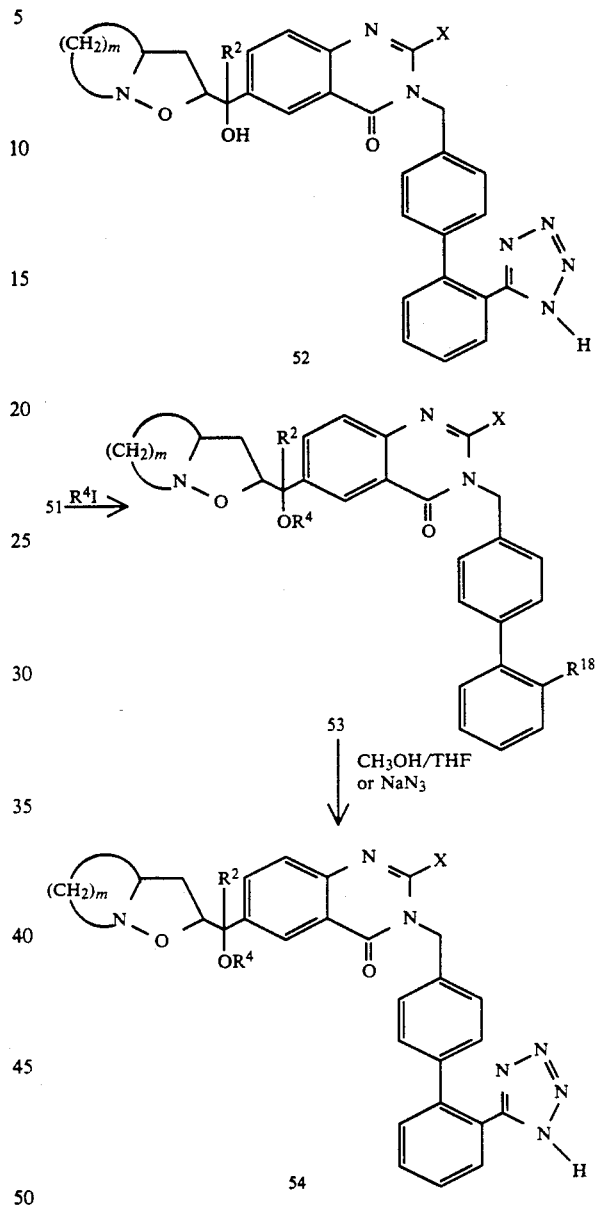

Reactions are performed in a solvent appropriate to the reagents and materials employed and suitable for the transformation being effected. It is understood by those skilled in the art of organic synthesis that the various functionalities present on the molecule must be consistent with the chemical transformations proposed. This may necessitate judgement as to the order of synthetic steps, protecting groups, if required, and deprotection conditions. Substituents on the starting materials may be incompatible with some of the reaction conditions. Such restrictions to the substituents which are compatible with the reaction conditions will be apparent to one skilled in the art.

Pharmaceutically suitable salts include both the metallic (inorganic) salts and organic salts; a list of which is given in *Remington's Pharmaceutical Sciences,* 17th Edition, pg. 1418 (1985). It is well known to one skilled in the art that an appropriate salt form is chosen based on physical and chemical stability, flowability, hydroscopicity and solubility. Preferred salts of this invention for the reasons cited above include potassium, sodium, calcium, magnesium and ammonium salts.

Some of the compounds of the hereinbefore described schemes have centers of asymmetry. The compounds may, therefore, exist in at least two and often more stereoisomeric forms. The present invention encompasses all stereoisomers of the compounds whether free from other stereoisomers or admixed with other stereoisomers in any proportion and thus includes, for instance, racemic mixture of isomers. The absolute configuration of any compound may be determined by conventional X-ray crystallography.

While the invention has been illustrated using the trityl protecting group on the tetrazole, it will be apparent to those skilled in the art that other nitrogen protecting groups may be utilized. Contemplated equivalent protecting groups include, benzyl, p-nitrobenzyl, propionititle or any other protecting group suitable for protecting the terazole nitrogen. Additionally, it will be apparent to those skilled in the art that removal of the various nitrogen protecting groups, other than trityl, may require methods other than dilute acid.

The compounds of this invention and their preparation are illustrated by the following non-limiting examples.

EXAMPLE 1

2-Butyl-6-(methyl)-4(1H)-quinazolinone

To 20.0 g of 2-amino-5-methylbenzoic acid is added 60 ml of valeric anhydride. The mixture is heated at reflux for 18 hours and then concentrated under reduced pressure. The resulting brown solid residue is dissolved in a mixture of 200 ml of 30% of ammonium hydroxide solution and 300 ml of ethyl alcohol. This mixture is heated at reflux for 5 hours and the allowed to cool to room temperature. After cooling, the precipitate is collected by filtration. The cake is washed with ethanol and water, then dried under vacuum to give 8.92 g of the quinazolinone as a white solid. CI MASS SPEC MH+ =217.

EXAMPLE 2

2-Butyl-6-iodo-4(1H)-quinazolinone

The method of Example 1 is used with 2-amino-5-iodobenzoic acid to prepare the desired product, m.p. 257°–258° C.

EXAMPLE 3

2-Butyl-6-(bromomethyl)-4(1H)-quinazolinone

To a suspension of 3.50 g of 6-methylquinazolinone in 100 ml of chloroform is added 3.39 g of N-bromosuccinimide and 0.25 g of benzoyl peroxide. The reaction mixture is heated at reflux for 18 hours and then filtered hot. A precipitate of 2.21 g of an inseparable mixture of the desired bromide and starting 6-methyl-quinazolinone is obtained and used in Example 4 without further purification.

EXAMPLE 4

2-Butyl-6-(hydroxymethyl)-4(1H)-quinazolinone

To a suspension of 2.0 g of impure 2-butyl-6-(bromomethyl)-4(1H)-quinazolinone (Example 3) in 35 ml of dimethylsulfoxide and 20 ml of water is added 1.0 g of potassium carbonate. The reaction mixture is heated at reflux for 6 hours, resulting in a complete solution. Upon cooling slowly to room temperature a white precipitate forms and is collected by filtration. The filter cake is purified by flash chromatography on silica gel, eluting with 9:1 chloroform-methanol to give 0.67 g of the desired product as a white solid. CI MASS SPEC 233(M+H).

EXAMPLE 5

2-Butyl-1,4-dihydro-4-oxo-6-quinazolinecarboxaldehyde

To a solution of 0.3 g of 2-butyl-6-(hydroxymethyl)-4(1H)-quinazolinone in 3.5 ml of dry N,N-dimethylformamide is added 1.7 g of pyridinium dichromate. The reaction mixture is stirred at room temperature for 16 hours and then poured into 125 ml of water. The resulting precipitate is removed by filtration and the filtrate extracted with 9:1 chloroform-methanol. The combined organic extracts are dried over magnesium sulfate, filtered and concentrated in vacuo and combined with the precipitate above. The combined solids are purified by flash chromatography on silica gel by eluting with 1:1 ethyl acetate-hexanes to give 0.27 g of the desired product. CI MASS SPEC 231(M+H).

EXAMPLE 6

2-Butyl-6-(1-hydroxyethyl)-4(1H)-quinazolinone

To a solution of 0.60 g of 2-butyl-1,4-dihydro-4-oxo-6-quinazolinecarboxaldehyde in 30 ml of dry tetrahydrofuran, cooled to 0° C. is added dropwise, 2.61 ml of a 30.M solution of methylmagnesium bromide in diethyl ether. The reaction is stirred at 0° C. for 30 minutes and then quenched with 10 ml of aqueous ammonium chloride. After diluting with 10 ml of water, the reaction mixture is extracted with 9:1 chloroform-methanol. The combined extracts are dried with magnesium sulfate, filtered and concentrated to yield 0.64 g of the desired product. CI MASS SPEC 247(MH+).

EXAMPLE 7

2-Butyl-6-(1-hydroxypropyl)-4(1H)-quinazolinone

To a solution of 0.25 g of 2-butyl-1,4-dihydro-4-oxo-6-quinazolinecarboxadehyde in 10 ml of dry tetrahydrofuran, cooled to 0° C., is added 1.63 ml of 2.0M ethyl magnesium bromide in tetrahydrofuran. The reaction mixture is stirred for 30 minutes at 0° C. and quenched with 20 ml of saturated ammonium chloride solution and 20 ml of water. The reaction mixture is extracted with 9:1 chloroform-methanol, dried over magnesium sulfate, filtered and evaporated in vacuo to give 0.26 g of the desired product. CI MASS SPEC 261(MH+).

EXAMPLE 8

2-Butyl-1,4-dihydro-4-oxo-6-quinazolinecarboxaldehyde

To a solution of 1.0 g of 2-butyl-6-iodo-4(1H)-quinazolinone and 0.355 g of tetrakis(triphenylphosphine)palladium in 15 ml of tetrahydrofuran and 5 ml of N,N-dimethylformamide, heated to 55° C. under an atmosphere of carbon monoxide is added a solution of 1.40 g tri-n-butyltin hydride in 2.5 ml of toluene over 6 hours via a syringe pump. After the addition is complete the reaction is allowed to cool to room temperature, diluted with brine and extracted with chloroform. The combined organics are concentrated in vacuo and the resulting residue triturated with ether. The precipitate is collected by filtration and purified by flash chromatography on silica gel, eluting with 1:1 ethyl acetate-hexanes to give 0.35 g of the desired product, m.p. 242°–244° C.

EXAMPLE 9

2-Butyl-6-[(trimethylsilyl)ethynyl]-4(1H)-quinazolinone

To a solution of 1.0 g of 2-butyl-6-iodo-4(1H)-quinazolinone 0.043 g of bis(triphenylphosphine) palladium (II) chloride and 5.8 mg of copper (I) iodide in 5.0 ml of N,N-dimethylformamide and 5.0 ml of triethylamine is added 0.36 g of (trimethylsilyl) acetylene. The resulting reaction mixture is heated at 45° C. for 1 hour and then 65° C. for 5 hours. Upon cooling, the reaction mixture is concentrated in vacuo and the residue purified by flash chromatography on silica gel, eluting with 1:3 ethyl acetate-hexane to yield 0.75 g of the desired product as a white solid. CI MASS SPEC 299(MH+).

EXAMPLE 10

2-Butyl-6-ethynyl-4(1H)-quinazolinone

To a solution of 0.70 g of 2-butyl-6-[(trimethylsilyl)ethynyl]-4(1H)-quinazolinone in 20 ml of methanol and 20 ml of tetrahydrofuran is added 10.0 ml of 1.0N sodium hydroxide solution. The reaction is stirred at room temperature for 2 hours and then diluted with 5% hydrochloric acid solution until the pH is 2. The resulting tan precipitate is collected filtration and dried in vacuo to yield 0.50 g of the desired product.
CI MASS SPEC 227(MH+).

EXAMPLE 11

6-Acetyl-2-butyl-4(1H)-quinazolinone

To a solution of 1.20 g of 2-butyl-6-ethynyl-4(1H)-quinazolinone in 90 ml of acetic acid is added 0.45 g of mercuric sulfate, 0.9 ml of water and 0.3 ml of sulfuric acid. The reaction mixture is heated at reflux for 5 hours, cooled to room temperature and quenched with 150 ml of water. The resulting mixture is concentrated in vacuo, diluted with 150 ml of water and extracted with 6:1 chloroform-methanol. The combined organics are dried over magnesium sulfate, filtered and concentrated in vacuo. The residue is purified by flash chromatography on silica gel, eluting with 1:1 ethyl acetate-hexanes to give 0.67 g of the desired product as a white solid. CI MASS SPEC 245(MH+).

EXAMPLE 12

2-Butyl-6-[hydroxy(tetrahydro-2-thienyl)methyl]-4(1H)-quinazolinone S,S-dioxide

A solution of 2 ml of tetramethylenesulfone in 20 ml of dry tetrahydrofuran is cooled to 0° C. and 6.4 ml of n-butyl lithium is added dropwise. After stirring at 0° C. for 30 minutes the mixture is cooled to −78° C. and 0.920 g of 2-butyl-1,4-dihydro-4-oxo-6-quinazolinecarboxaldehyde added in small portions. The reaction mixture is stirred at −78° C. for 4.5 hours and then allowed to warm to 0° C. The reaction mixture is quenched with 20 ml of saturated ammonium chloride and stirred for 30 minutes. The reaction mixture is concentrated under vacuum and extracted with three 50 ml portions of ethyl acetate. The combined extracts are dried with anhydrous sodium sulfate and evaporated to a residue which is heated with 1:1 ethyl acetate-hexanes to afford 0.580 g of solid upon cooling. The solid is purified by chromatography on silica gel using 3:1 ethyl acetate-hexanes to give 0.360 g of the desired product, m.p. 207°–209° C.

EXAMPLE 13

2-Butyl-6-[hydroxy(tetrahydro-2-thienyl)methyl-3-[[2'-[1-(triphenylmethyl)-1H-tetrazol-5-yl][1,1'-biphenyl]-4-yl]methyl-3-quinazolinone S,S-dioxide isomer 1

EXAMPLE 14

2-Butyl-6-[hydroxy(tetrahydro-2-thienyl)methyl]-3[[2¹-[1-(triphenylmethyl)-1H-tetrazol-5-yl][1,1'-biphenyl]-4-yl]methyl]-3-quinazolinone S,S-dioxide isomer 2

A solution of 0.350 g of 2-Butyl-6-[hydroxy(tetrahydro-2-thienyl)methyl]-4(1H)-quinazolinone S,S-dioxide in 3 ml of dry N,N-dimethylformamide is stirred under argon while 38 mg of lithium methoxide is added followed by 1.115 g of 5-[4'-(bromomethyl)[1,1'-biphenyl]-2-yl]-1-(triphenylmethyl)-1H -tetrazole. Following a complete solution, 0.300 g of sodium iodide is added and the reaction mixture heated in an oil bath at 55°-60° for 18 hours. The bath is removed and the reaction mixture stirred for an additional 30 minutes. The reaction mixture is concentrated in vacuo to a residue which is dissolved in 50 ml of ethyl acetate. The organic layer is washed with 20 ml of water and 20 ml of brine, dried with anhydrous Na$_2$SO$_4$ and evaporated in vacuo to afford 1.5 g of a dark brown foam. The diastereomers are separated on 85 g of silica gel using a 3.5 cm×38 cm column by elution with 1:1 and 2:1 ethyl acetate-hexanes taking 50 ml fractions to give from fractions 26–37, 220 mg of the first diastereomer as a pale foam pmr (CDCl$_3$) δ 0.87 (m, 3H, —CH$_3$), 5.11 (m, 1H, —CHOH), 5.33 (S, 2H, NCH$_2$—and from fractions 40–45, 200 mg of the second diastereomer as a pale foam pmr (CDCl$_3$) δ 0.89 (m, 3H,—CH$_3$), 5.64 (m, 1H, —CHOH), 5.33 (S, 2H, NH$_2$—).

EXAMPLE 15

2-Butyl-6-[hydroxy(tetrahydro-2-thienyl)methyl-3-[[2'-(1H-tetrazol-5-yl)[1,1'-biphenyl]-4-yl]methyl]-4(3H)-quinazolinone S,S-dioxide isomer 1

A solution of 0.220 g of 2-Butyl-6-[hydroxy(tetrahydro-2-thienyl)methyl-3-[[2'-[1-(triphenylmethyl)-1H-tetrazol-5-yl][1,1'-biphenyl]-4-yl]methyl]-3-quinazolinone S,S-dioxide isomer 1 in 10 ml of methyl alcohol and 2 ml of tetrahydrofuran is refluxed for 18 hours under argon. The volatiles are evaporated and the residue dissolved in ethyl acetate containing a drop of methyl alcohol. The solution is applied to silica gel and eluted with 1:1 ethyl acetate-hexanes to afford 110 mg of the desired product as a pale solid, m.p. 120°–128° C., pmr (CDCl$_3$) δ 0.89 (t, 3H, CH$_3$), 5.33 (q, 2H, NCH$_2$—), 5.53 (S,1H).

EXAMPLE 16

2-Butyl-6-[hydroxy(tetrahydro-2-thienyl)methyl-3-[2'-(1H-tetrazol-5-yl)[1,1'biphenyl]-4-yl]methyl]-4(3H)-quinazolinone S, S-dioxide, isomer 2

A solution of 0.200 g of 2-Butyl-6-[hydroxy(tetrahydro-2-thienyl)methyl-3-[[2'-[1-(triphenylmethyl)-1H-tetrazol-5-yl][1,1'-biphenyl]-4-yl]methyl]-3-quinazolinone S,S-dioxide isomer 2 in 10 ml of methyl alcohol and 2 ml of tetrahydrofuran is refluxed for 18 hours under argon. The volatiles are evaporated and the residue dissolved in ethyl acetate containing a drop of methyl alcohol. The solution is applied to silica gel and eluted with 1:1 ethyl acetate-hexanes to afford 110 mg of the desired product as a pale solid, m.p. 208°–220° C. pmr (CDCl$_3$) δ 0.89 (t, 3H, CH$_3$), 5.03 (d, 1H), 5.33 (S, 2H, NCH$_2$—).

EXAMPLE 17

2-Butyl-6-(2-furanylhydroxymethyl)-4(1H)-quinazolinone

To a stirred solution of 7.88 ml of furan in 80 ml of dry tetrahydrofuran is cooled at 0° C. and 47.8 ml of n-butyl lithium (2.5 M in hexanes) is added dropwise. Stirring is continued for 1 hour at 0° C. and the mixture allowed to warm to room temperature. The reaction mixture is cooled to −78° C. and 5.0 g of 2-butyl-1,4-dihydro-4-oxo-6-quinazolinecarboxaldehyde added rapidly. The reaction mixture is stirred for 1.5 hours at −78° C., quenched with 100 ml of saturated ammonium chloride, allowed to warm to room temperature and the volatiles removed in vacuo. The reaction mixture is diluted with 500 ml of ethyl acetate and washed with water, 2N citric acid, 1M sodium bicarbonate and brine. The organic layer is dried and evaporated to a residue which crystallizes from ethyl acetate to afford 3.75 g of the desired product, m.p. 183°–185° C. An additional 700 mg of the desired product is obtained from the filtrate as white crystals m.p. 183°–185° C. Fab Mass Spec 299 (M+H).

EXAMPLE 18

2-Butyl-6-(2-furanylhydroxymethyl)-3-[2'-[1-(triphenylmethyl)-1H-tetrazol-5-yl][1,1'biphenyl]-4-yl]methyl-4(3H)-quinazolinone A solution of 500 mg of 2-butyl-6-(2-furanylhydroxymethyl)-4(1H)-quinazolinone in 8 ml of N,N-dimethylformamide is stirred while 63.64 mg of lithium methoxide is added followed by 1.87 g of 5-[4'-(bromomethyl)[1,1'biphenyl]-2-yl]-1-(triphenylmethyl)-1H-tetrazole. After stirring for 10 minutes, 251.25 mg of sodium iodide is added followed by heating in an oil bath at 55° C. for 18 hours. The volatiles are evaporated in vacuo to a residue which partitioned between ethyl acetate and water. The organic layer is washed with brine, dried with anhydrous Na$_2$SO$_4$ and the volatiles evaporated to afford 2.0 g of a dark residue. The residue is purified by chromatography on silica gel with (2.25:1)hexanes:ethyl acetate as solvent to afford 815 mg of the desired product as a white foam. Fab Mass Spec 797 (M+Na).

EXAMPLE 19

2-Butyl-6-(2-furanylmethoxymethyl)-3-[[2'-[1-(triphenylmethyl)-1H-tetrazol-5-yl][1,1'-biphenyl]-4-yl]methyl-4(3H)-quinazolinone A mixture of 82.3 mg of 60% sodium hydride in oil (hexane washed) in 3 ml of tetrahydrofuran is cooled to 0° C. and a solution of 800 mg of 2-Butyl-6-(2-furanylhydroxymethyl)-3-[[2'-[1-(triphenylmethyl)-1H-tetrazol-5-yl][1,1'biphenyl]-4-yl]methyl-4(3H)-quinazolinone in 2 ml of tetrahydrofuran is added dropwise. After stirring for 10 minutes, 0.643 ml of methyl iodide is added. The cooling bath is removed and the reaction mixture stirred for 18 hours at room temperature. The volatiles are removed and the residue partitioned between ethyl acetate and water. The organic layer is washed with brine, dried with anhydrous Na$_2$SO$_4$ and evaporated to dryness to give 730 mg of the desired product as a light orange foam. Fab Mass Spec 811 (M+Na) 789 (M+H).

EXAMPLE 20

2-Butyl-6-(2-furanylmethoxymethyl)-3-[[2'-(1H-tetrazol-5-yl][1,1'-biphenyl]-4-yl]methyl-4(3H)-quinazolinone To a solution of 250 mg of 2-Butyl-6-(2-furanylmethoxymethyl)-3-[[2'-[1-(triphenylmethyl) -1H-tetrazol-5-yl][1,1'biphenyl]-4-yl]methyl-4(3H)-quinazolinone in 1 ml of tetrahydrofuran is added 5 ml of methanol followed by heating at reflux for 18 hours. The volatiles are evaporated to a residue which is purified by chromatography on silica gel with 1:1 ethyl acetate-hexanes as eluent to afford 145 mg of the desired product as a white foam. Mass Spec MSFABL 569 (M+Na) Pmr (DMSO) 0.87 (t, 3H, CH$_3$), 3.34 (S, 3H, OCH$_3$).

EXAMPLE 21

2-Butyl-6-methoxy(tetrahydro-2-furanyl)methyl-3-[[2'-[1-(triphenylmethyl)-1H-tetrazol-5-yl][1,1'-biphenyl]-4-yl]methyl-4(3H)-quinazolinone, isomer 1

EXAMPLE 22

2-butyl-6-[methoxy(tetrahydro-2-furanyl)methyl-3-[[2'-[1-(triphenylmethyl)-1H-tetrazol-5-yl] [1,1'-biphenyl]-4-yl]methyl]-4(3e,uns/H/ )-quinazolinone isomer 2

A mixture of 440 mg of 2-butyl-6-(2-furanylmethoxymethyl)-3-[[2'-[1-(triphenylmethyl)-1H-tetrazol-5-5-yl][1,1-biphenyl]-4-yl]methyl-4(3H)-quinazolinone and 240 mg of 5% rhodium-on-aluminum powder in 25 ml of ethyl acetate is shaken under 35 psi of hydrogen for 4 hours. An addition 1.0 g of catalyst and 40 ml of ethyl acetate is added followed by shaking under 35 psi of hydrogen for 18 hours. The reaction mixture is filtered, the cake washed with ethyl acetate and the combined filtrates evaporated to a residue. The residue is purified on a thick layer silica gel chromatography plates with 1:1 ethyl acetate-hexanes as solvent to give 102 mg of the first desired isomer product as a white foam and 150 mg of the second desired isomer product as a off-white foam. (Example 21) pmr (CDCl$_3$) & 0.90 (t, 3H, CH$_3$), 3.25 (S, 3H, OCH$_3$) (Example 22) pmr (CDCl$_3$) δ 0.90 (t, 3H, CH$_3$), 3.25 (S, 3H, OCH$_3$).

EXAMPLE 23

2-Butyl-6-[methoxy(tetrahydro-2-furanyl)methyl-3-[[2'-(1H-tetrazol-5-yl)[1,1'-biphenyl]-4-yl]-methyl]-4(3e,uns/H/ )-quinazolinone isomer 1

To a mixture of 90 mg 2-Butyl-6-[methoxy(tetrahydro-2-furanyl)methyl]-3-[[2'-[1-(triphenylmethyl)-1e,uns/H/ -tetrazol-5-yl][1,1'-biphenyl]-4-yl]methyl]-4(3H) -quinazolinone, is added 3.5 ml of methanol followed by reflux for 18 hours. The volatiles are evaporated and the residue is purified on preparative silica gel plates with 2:1 ethyl acetate-methanol as solvent. The product is collected in ethyl acetate, filtered through diatomaceous earth and the filtrate evaporated to give 59 mg of the desired product as off-white solid. Mass Spec MSFABL 595 (M+2Na-H).

EXAMPLE 24

2-Butyl-6-[methoxy(tetrahydro-2-furanyl)methyl -3-[[2'-(1H-tetrazol-5-yl)[1,1'-biphenyl]-4-yl]methyl] 4(3H)-quinazolinone isomer 2

To a solution of 135 mg (second isomer) 2-butyl-6-[methoxy(tetrahydro-2-furanyl)methyl]-3-[[2'-[1-(triphenylmethyl)-1H-tetrazol-5-yl][1,1'-biphenyl]-4-yl]methyl]-4(3H)-quinazolinone isomer 2 in 1 ml of tetrahydrofuran is added 5 ml of methanol followed by reflux for 18 hours. The volatiles are evaporated to a residue which is chromatography on preparative silica gel plates by elution with 2:1 ethyl acetate-methanol. The desired product is collected in ethyl acetate, filtered through diatomaceous earth and the filtrate evaporated to give 68 mg of the desired product as an off-white solid. Mass Spec MSFABL 595 (M+2Na-H).

EXAMPLE 25

2-Butyl-6-[hydroxy(tetrahydro-2-furanyl)methyl-4(1H)-quinazolinone stereoisomers To a mixture of 300 mg of 2-butyl-6-(2-furanylhydroxymethyl)-4(1H)-quinazolinone in 10 ml of ethyl acetate is added 100 mg of 5% rhodium-on-alumina powder. The reaction mixture is shaken under 35 pounds of hydrogen pressure for 2 hours. An additional 3 ml of ethyl alcohol and 50 mg of 5% rhodium-on-alumina is added and the reaction mixture shaken under 35 pounds of hydrogen pressure for 2 hours. The reaction mixture is filtered through diatomaceous earth and the filtrate evaporated to a residue which forms 300 mg of a semisolid from a solvent mixture of ethyl acetate-hexanes. The semi-solid is purified by chromatography on silica gel preparative plates with 2:1 ethyl acetate-hexanes as solvent to give 50 mg of the desired product as a white solid. Pmr (CDCl$_3$) δ 0.98 (t, 3H, —CH$_3$), 1.44 (m, 2H), 1.8 (m,6H), 2.64 (m, 2H).

EXAMPLE 26

2-Butyl-6-[hydroxy(tetrahydro-2-furanyl)methyl-4(1H)-quinazolinone stereoisomers To a solution of 130 mg of 2-butyl-6-(2-furanylhydroxymethyl)-4(1H)-quinazolinone in 3 ml of methanol is added 110 mg of ammonium formate followed by stirring for 10 minutes. Added 65 mg of 10% Pd/c in 1.5 ml of water beneath the surface of the solvent without stirring. Stirring is continued for an additional hour. Another 130 mg of 10% Pd/c is added and the reaction mixture stirred for an additional hour. An additional 150 mg of ammonium formate and 150 mg of 10% Pd/c in 1.5 ml of water are added and the reaction mixture stirred for an additional 2 hours, filtered through diatomaceous earth and the filtrate evaporated to a residue. The residue is crystallized from ethyl acetate-hexanes to give 92 mg of off-white crystals m.p. 206°-208° C. Pmr (CDCl$_3$) δ 0.98 (t,3H, —CH$_3$), 1.44 (m, 2H), 1.8 (m, 6H).

EXAMPLE 27

2-Butyl-6-hydroxy(tetrahydro-2-furanyl)methyl]-3-[[2'-[1-(triphenylmethyl)-1H-tetrazol -5-yl] [1,1'-biphenyl-4-yl]methyl-4(3H)-quinazolinone stereoisomers To 12 mg of hexane washed 60% sodium hydride in mineral oil is added 2 ml of N.N-dimethylformamide followed by 80 mg of 2-butyl-6-[hydroxy(tetrahydro-2-furanyl)methyl]-4(1H)-quinazolinone stereoisomers with stirring at room temperature for 1 hour. After cooling to 0° C., 176.7 mg of 5-[4'-bromomethyl)[1,1'-biphenyl]-2-yl]-1-(triphenylmethyl) -dimethylformamide is added followed by removal of the cooling bath and heating the reaction mixture in an oil bath at 55° for 18 hours. An additional 177 mg of 5-[4'-(bromomethyl)[1,1'-biphenyl]-2-yl]-1-(triphenylmethyl)-1H-tetrazole and 47.52 mg of sodium iodide is added followed by stirring and heating at 55° C. for 18 hours. The volatiles are removed in vacuo to a residue which is dissolved in ethyl acetate, washed with water, brine, dried with anhydrous Na$_2$SO$_4$ and evaporated to a residue. The residue is chromatographed on silica gel preparative plates with 2:1 ethyl acetate-hexanes as solvent to afford 95 mg of the desired product as a white solid. Pmr (CDCl$_3$) δ 0.90 (t, 3H, CH$_3$), 5.3 (S, 2H, —NCH$_2$—).

EXAMPLE 28

2-Butyl-6-[hydroxy(tetrahydro-2-furanyl)methyl-3-[[2'-(1H-tetrazol-5-yl)[1,1'-biphenyl]-4-yl]methyl]-4(3H)-quinazolinone To a solution of 85 mg of 2-Butyl-6-[hydroxy(tetrahydro-2-furanyl)methyl]-3-[[2'[1-(triphenylmethyl-1H-tetrazol-5-yl][1,1'-biphenyl]-4-yl]methyl-4(3H)-quinazolinone stereoisomers in 0.7 ml of tetrahydrofuran is added 3.5 ml of methanol followed by heating at reflux for 18 hours. The volatiles are removed and the residue is chromatography on thick layer silica gel plates with 7% acetic acid in ethyl acetate to give 45 mg of the desired product as a white solid. Mass Spec MSFABL 559 (M+Na).

EXAMPLE 29

2-Butyl-6-[hydroxy(1-methyl-2-oxo-3-pyrrolidinyl)methyl]-4(1H)-quinazolinone To a solution of 0.834 ml of 1-methyl-2-pyrrolidinone in 10 ml of tetrahydrofuran is added dropwise with stirring 8.69 ml of lithium bis(trimethylsilyl)amide (1.0M in tetrahydrofuran) at −78° C. Following complete addition, 500 mg of 2-butyl-1,4-dihydro-4-oxo-6-quinazolinecarboxaldehyde is rapidly added and the reactants stirred at −78° C. for 4 ½ hours. The reaction mixture is quenched with 10 ml of saturated ammonium chloride and allowed to warm to room temperature followed by evaporation of the volatiles in vacuo to a residue. The residue is diluted with 5 ml of water and extracted with ethyl acetate. The extract is washed with water, brine and dried with anhydrous Na$_2$SO$_4$.

The aqueous layer is extracted with methylene chloride and the organic layer dried with anhydrous Na$_2$SO$_4$. The combined organic layers are evaporated to give 800 mg of a residue which is chromatographed on silica gel preparative plates with 20% methanol in ethyl acetate to give 465 mg of the desired product as a reddish oil. Mass Spec MSFABL 352 (M+Na).

EXAMPLE 30

2-Butyl-6-hydroxy(1-methyl-2-oxo-3-pyrrolidinyl)-methyl-3-[[2'-[1-(triphenylmethyl) -1H-tetrazol-5-yl] 1,1'-biphenyl]-4-yl]methyl]-4(3H)-quinazolinone isomer 1

EXAMPLE 31

2-Butyl-6-hydroxy(1-methyl-2-oxo-3-pyrrolidinyl)-methyl-3-[[2'-[1-(triphenylmethyl)-1H-tetrazol-5-yl] [1,1'-biphenyl]-4-yl]methyl]-4(3H-quinazolinone isomer 2

This reaction is performed under the same conditions as Example 18 using 430 mg of 2-Butyl-6-[hydroxy(1-methyl-2-oxo-3-pyrrolidinyl)-methyl ]-4(1H)-quinazolinone, 1.45 g of 5-[4'-(bromomethyl)[1,1'-biphenyl]-2-yl]-1-(triphenylmethyl)1H-tetrazole, 49.6 mg of lithium methoxide and 195 mg of sodium iodide in 7 ml of N,N-dimethylformamide to give 1.0 g of residue. The residue is purified by high pressure liquid chromatography (HPLC) on silica gel with ethyl acetatehexanes as solvent to give 520 mg of the first isomer as a light brown foam and 230 mg of the second isomer as a light brown foam. Pmr (CDCl$_3$) δ 0.87 (m, 3H, CH$_3$), 5.11 (m, 1H, —CHOH), 5.33 (S, 2H, —NCH$_2$—).

EXAMPLE 32

2-Butyl-6-[hydroxy(1-methyl-2-oxo-3-pyrrolidinyl)methyl]-3-[[2'-(1e,uns/H/ -tetrazol-5-yl)[1,1'-biphenyl]-4-yl]methyl]-4(3H)-quinazolinone isomer 1

To a solution of 200 mg of 2-Butyl-6-[hydroxy(1-methyl-2-oxo-3-pyrrolidinyl)methyl-3-[[2'-[1-(triphenylmethyl)-1H-tetrazol-5-yl][1,1'-biphenyl]-4-yl]methyl]-4(3e,uns/H/ )-quinazolinone isomer 1 in 1 ml of tetrahydrofuran is added 5 ml of methanol followed by heating at reflux for 18 hours. The volatiles are evaporated to a residue which is purified by chromatography on silica gel preparative plates using 1.5:1 ethyl acetate-hexanes to give 105 mg of the desired product as a white foam. Mass Spec MSFABL 563.

EXAMPLE 33

2-Butyl-6-[hydroxy(1-methyl-2-oxo-3-pyrrolidinyl)-methyl-3-[[2'-(1H-tetrazol-5-yl)[1,1'-biphenyl]-4-yl]methyl]-4(3H)-quinazolinone isomer 2

To a solution of 490 mg of 2-Butyl-6-[hydroxy(1-methyl-2-oxo-3-pyrrolidinyl)-methyl-3-[[2'-[1-(triphenylmethyl)-1H-tetrazol-5-yl][1,1'-biphenyl]-4-yl]methyl]-4(3H)-quinazolinone isomer 2 in 2.5 ml of tetrahydrofuran is added 12.5 ml of methanol followed by heating at reflux for 18 hours. The volatiles are evaporated to a residue which is purified by chromatography on silica gel preparative plates with 1.5:1 ethyl acetate-hexanes as solvent to afford 193 mg of the desired product as a white foam. Mass Spec MSFABL 586 (M+Na).

EXAMPLE 34

2-Butyl-6-hydroxy(1-methyl-2-oxo-3-piperidinyl)methyl]-4(1H)-quinazolinone stereoisomers To a stirred solution of 3.95 ml of 1-methyl-2-piperidone in 40 ml of tetrahydrofuran at −78° C. under argon is added dropwise 34.8 ml of lithium bis(trimethylsilylamide)(1.0M in tetrahydrofuran) followed by stirring 1.5 hours. To the reaction mixture is added portionwise 2.0 g of 2-butyl-1,4-dihydro-4-oxo-6-quinazolinecarboxaldehyde and stirring continued at −78° C. for 4 hours. The temperature is raised to 0° C. and stirring continued for an additional hour. The reaction mixture is quenched with 50 ml of saturated ammonium chloride and the volatiles evaporated to a residue which is diluted with 20 ml of water and extracted with ethyl acetate. The organic layer is washed with water and brine then dried with anhydrous sodium sulfate and evaporated to give 5.0 g of an oily residue which is purified by chromatography on silica gel with 1:1 ethyl acetate-hexanes and then 2:1 ethyl acetate-hexanes as solvent to give 2.8 g of the desired product as an oily solid. Pmr (CDCl$_3$) δ 1.0 (t, 3H, CH$_3$), 1.5 (q, 2H, —CH$_2$—CH$_3$), 1.8 (m, 4H), 2.8 (m, 2H), 2.96 (S, 3H, NCH$_3$).

EXAMPLE 35

2-Butyl-6-[hydroxy(1-methyl-2-oxo-3-piperidinyl)methyl]-3-[[2'-[1-triphenylmethyl)-1H-tetrazol-5yl][1,1'-biphenyl]-4-yl]methyl-4(3H)-quinazolinone isomer 1

EXAMPLE 36

2-Butyl-6-[hydroxy(1-methyl-2-oxo-3-piperidinyl)methyl]-3-[[2'-[1-(triphenylmethyl)-1H-tetrazol-5-yl][1,1'-biphenyl]-4-yl]methyl-4(3H) -quinazolinone isomer 2

To a stirred solution of 2.60 g of 2-Butyl-6-[hydroxy(1-methyl-2-oxo-3-piperidinyl)-methyl]4(1H)-quinazolinone stereoisomers in 40 ml of N,N-dimethylformamide under argon is added 287.4 mg of lithium methoxide followed by 8.44 g of 5-[4'-(bromomethyl)-[1,1'-biphenyl]-2-yl]-1-(triphenylmethyl) -1H-tetrazole. After stirring for 10 minutes, 1.13 g of sodium iodide is added and the reaction mixture heated in an oil bath of 55° C. for 22 hours. The volatiles are evaporated in vacuo to a residue which is dissolved in ethyl acetate, washed with water then brine. The organic layer is dried with anhydrous Na and evaporated to give 10.0 g of a residual oily solid. The residue is purified by high pressure liquid chromatography(HPLC) on silica gel using a solvent system of 7.5L of ethyl acetate and 0.5L of hexanes. The first desired product totals 1.29 g and is a white foam (isomer 1). The second desired product totals 1.2 g and is a yellow foam (isomer 2). (Example 35) Mass Spec MSFABL 842 (M+Na) (Example 36) Mass Spec MSFABL 1.842 (M+Na).

EXAMPLE 37

2-Butyl-6-hydroxy(1-methyl-2-oxo-3-piperidinyl)methyl]-3-[[2'-(1H-tetrazol-5-yl)[1,1'-biphenyl]-4-yl]methyl]-4(3H)-quinazolinone isomer 1

To a solution of 400 mg of 2-butyl-6-[hydroxy(1-methyl-2-oxo-3-piperidinyl)methyl]-3[[2'-[1-(triphenylmethyl)-1H-tetrazol-5-yl][1,1'biphenyl]-4-yl]methyl-4(3H)-quinazolinone isomer 1 in 1.5 ml of tetrahydrofuran is added 7.5 ml of methanol followed by heating at reflux for 18 hours. The volatiles are evaporated to a residue which is purified by chromatography on preparative silica gel plates with 1.5:1 ethyl acetate-methanol as solvent to afford 185 mg of the desired product as a white foam. Mass Spec MSFABL 600 (M+Na).

EXAMPLE 38

2-Butyl-6-hydroxy(1-methyl-2-oxo-3-piperidinyl)methyl-3-[[2'-(1H-tetrazol-5-yl)[1,1'-biphenyl]-4-yl]methyl-4(3H)-quinazolinone isomer 2

To a solution of 400 mg of 2-butyl-6-[hydroxy-(1-methyl-2-oxo-3-piperidinyl)-methyl]-3-[[2'(1H-tetrazol-5-yl)[1,1'-biphenyl]-4-]methyl]-4(3H)quinazolinone isomer 2 in 1.5 ml of tetrahydrofuran is added 7.5 ml of methanol followed by heating at reflux for 18 hours. The volatiles are evaporated to a residue which is purified by chromatography or preparative silica gel plates with 1.5:1 ethyl acetate-methanol to afford 188 mg of the desired product as a white foam. Mass spec MSFABL 600 (M+Na).

EXAMPLE 39

2-Butyl-6-methoxy(1-methyl-2-oxo-3-piperidinyl)methyl]-3-[[2'-[1-(triphenylmethyl)-1H-tetrazol-5-yl][1,1'-biphenyl]-4-yl]methyl]-4(3H)-quinazolinone isomer 1

EXAMPLE 40

2-Butyl-6-methoxy(1-methyl-2-oxo-3-piperidinyl)methyl]-3-[[2'-[1-(triphenylmethyl)-1H-tetrazol-5-yl][1,1'-biphenyl]-4-yl]methyl]-4(3H)-quinazolinone isomer 2

To 73.81 mg of 60% sodium hydride in oil (washed with hexanes) is added 4 ml of tetrahydrofuran and the resulting suspension cooled to 0° C. To the suspension is added dropwise a solution of 760 mg of 2-butyl-6-[hydroxy(1-methyl-2-oxo-3-piperidinyl)methyl]-3-[[2'-[1-(triphenylmethyl)-1H-tetrazol-5-yl]-[1,1'-biphenyl]-4-yl]methyl-4(3H)-quinazolinone isomer 1 in 3 ml of tetrahydrofuran. After stirring for 10 minutes, 577 ul of methyl iodide is slowly added, the cooling bath removed and the reaction mixture stirred at room temperature for 18 hours. The volatiles are evaporated to give a residue which is purified by chromatography on preparative silica gel plates with ethyl acetate as solvent to afford 137 mg of a white foam and 360 mg of a white foam. (Example 39) Mass Spec MSFAB 856 (M+Na) (Example 40) Mass Spec MSFABL 856 (M+Na).

EXAMPLE 41

2-Butyl-6-methoxy(1-methyl-2-oxo-3-piperidinyl)methyl]-3-[[2'-[1-(triphenylmethyl)-1H-tetrazol-5-yl][1,1'-biphenyl]-4-yl]methyl]-4(3H) quinazolinone To 57.31 mg of 60% sodium hydride in oil (washed with hexanes) is added 3 ml of tetrahydrofuran and the resulting suspension cooled to 0° C. To the suspension is added dropwise a solution of 590 mg of 2-butyl-6-[hydroxy(1-methyl-2-oxo-3-piperidinyl)methyl-3-[[2'-[1-(triphenylmethyl) -1H-tetrazol-5-yl][1,1'-biphenyl]-4-yl]methyl-4(3H)-quinazolinone in 2 ml of tetrahydrofuran. After stirring for 10 minutes, 448 ul of methyl iodide is slowly added, the cooling bath removed and the reaction mixture stirred at room temperature for 48 hours. The volatiles are removed under vacuum and, the residue dissolved in ethyl acetate, is washed with water, brine and then dried with anhydrous $Na_2SO_4$. The solvent is evaporated to give 550 mg of a yellow foam which is purified by chromatography on preparative silica gel plates with 10 methanol in ethyl acetate to give 458 mg of the desired product as a white foam. Mass Spec MSFABL 856 (M+Na).

EXAMPLE 42

2-Butyl-6-methoxy(1-methyl-2-oxo-3-piperidinyl)methyl]-3-[[2'-1H-tetrazol-5-yl)[1,1'-biphenyl]-4-yl]methyl-4(3H)-quinazolinone isomer 1

To a solution of 400 mg of 2-butyl-6[methoxy(1-methyl-2-oxo-3-piperidinyl)methyl]-3-[[2 '[1-(triphenylmethyl)-1H-tetrazol-5-yl][1,1'-biphenyl]4-yl]methyl]-4(3H)-quinazolinone in 1.5 ml of tetrahydrofuran is added 7.5 ml of methanol followed by heating at reflux for 18 hours. The volatiles are evaporated and the residue is purified by chromatography on silica gel plates with 2:1 ethyl acetate methanol to give 248 mg of the desired product as a white foam. Mass Spec MSFABL 614 (M+Na).

EXAMPLE 43

2-Butyl-6-[methoxy(1-methyl-2-oxo-3-piperidinyl)methyl]-3-[[2'-(1H-tetrazol-5-yl)[1,1'-biphenyl]-4-yl]methyl]-4(3H)-quinazoline isomer 2

To a solution of 350 mg of 2-butyl-6[methoxy-(1-methyl-2-oxo-3-piperidinyl)methyl]-3-[[2'[1-(triphenylmethyl)-1H-tetrazol-5-yl][1,1-biphenyl]4-yl]methyl]-4(3H)-quinazolinone in 1 ml of tetrahydrofuran is added 5 ml of methanol followed by heating at reflux for 18 hours. The volatiles are removed and the residue purified by chromatography on silica gel plates with 2:1 ethyl acetate-hexanes to afford 174 mg of the desired product as a white foam. Mass Spec MSFABL 614 (M+Na).

EXAMPLE 44

2-Butyl-6-[1-hydroxy-1-(1-methyl-2-oxo-3-pyrrolidinyl)ethyl]-4(1H)-quinazolinone stereoisomers To a stirred solution of 3.14 ml of 1-methyl-2-pyrrolidinone in 120 ml of dry tetrahydrofuran at −78° C. is added dropwise 32 8 ml of lithium bis(trimethylsilylamide)(1.0M in tetrahydrofuran followed by stirring for 1.5 hours. To the reaction mixture is added portionwise 8.07 g of cerium chloride and the mixture stirred for 1 hour at −70° C. To the mixture is added portionwise 2.0 g of 6-acetyl-2-butyl-4(1H)quinazolinone and the mixture stirred 5 hours at −70° C. The mixture is allowed to warm to 0° C. and stand overnight (0° C.). After addition of 60 ml of saturated ammonium chloride, the mixture is allowed to warm to room temperature and is filtered through diatomaceous earth which is washed with ethyl acetate. The filtrate is concentrated, the residue dissolved in ethyl acetate and the solution washed with 80 ml each of water, and brine and dried ($Na_2SO_4$). The solvent is removed and the solid purified by high pressure liquid chromatography (HPLC) on silica with 2% methanol in ethyl acetate as solvent to give 2.21 g of product as a white glass. Anal. Calcd. for $C_{19}H_{25}N_3O_3$ ½$H_2O$:C,64.8;H,7.4; N,11.9. Found:C,64.1;H,7.6;N,11.9. Mass Spec MSFABL 344 (M+H).

EXAMPLE 45

2-Butyl-6-1-hydroxy-1-(1-methyl-2-oxo-3-pyrrolidinyl)ethyl]-3-[[2'-[1-(triphenylmethyl)-1H-tetrazol-5-yl][1,1'-biphenyl]-4-yl]methyl-4(3H)-quinazolinone isomer 1

Example 46

2-Butyl-6-[1-hydroxy-1-(1-methyl-2-oxo-3-pyrrolidinyl)ethyl]-3-[[2'-[1-(triphenylmethyl)-1H-tetrazol-5-yl][1,1'-biphenyl]-4-yl]methyl-4(3H)-quinazolinone isomer 2

To a solution of 2.0 g 2-butyl-6-[1-hydroxy-1-(1-methyl-2-oxo-3-pyrrolidinyl)ethyl]-4 (1H)-quinazolinone stereoisomers in 20 ml of N,N-dimethylformamide is added 221 mg of lithium methoxide followed by 6.5 g of 5-[4'-(bromomethyl)-[1,1'-biphenyl]-2-yl]-1-(triphenylmethyl)-1H-tetrazole. After stirring 10 minutes, 873 mg of sodium iodide is added and the mixture heated in an oil bath at 50° overnight. The volatiles are evaporated in vacuo to a residue which is dissolved in 250 ml of ethyl acetate which is washed with water and then brine. The organic layer is dried (Na$_2$SO$_4$) and the solvent removed to give 8.0 g of a residue. The residue is purified by high pressure liquid chromatography (HPLC) on silica gel with a solvent system of ethyl acetate-hexanes (3:1). The first desired product totals 2.1 g and is a light yellow foam (isomer 1). The second more polar product totals 1.95 g and is a light yellow foam. (Example 45) Mass Spec MSFABL 820 (M+H); (Example 46) Mass Spec MSFABL 820 (M+H).

EXAMPLE 47

2-Butyl-6-1-hydroxy-1-(1-methyl-2-oxo-3-pyrrolidinyl)ethyl]-3-[[2'-[1H(tetrazol-5yl)-[1,1'-biphenyl]-4-yl]methyl-4(3H)-quinazolinone isomer 1

A solution of 1.8 g of Example 45, isomer 1, in 6 ml of tetrahydrofuran and 30 ml of methanol is refluxed for 18 hours and the solvent removed. The residue is purified by high pressure liquid chromatography (HPLC) on silica gel with a solvent system of ethyl acetate-hexanes (3:1) to give 370 mg of product as a foam. Mass Spec MSFABL 600 (M+Na).

EXAMPLE 48

2-Butyl-6-1-hydroxy-1(1-methyl-2-oxo-3-pyrrolidinyl)ethyl]-3-[[2'-(1H-tetrazol-5-yl)[1,1'-biphenyl]-4-yl]methyl-4(3H)-quinazolinone isomer 2

A solution of 1.6 g of Example 46 in 6 ml of tetrahydrofuran and 30 ml of ethanol is refluxed for 18 hours and the solvent removed. The residue is purified by column chromatography on silica gel with 10% methanol in ethyl acetate as solvent to give 780 mg of product as an off-white foam. Mass Spec MSFABL 600 (M+Na).

EXAMPLE 49

2-Butyl-6-1-hydroxy(1-methyl-2-oxo-3-piperidinyl)ethyl]-4(1H)-quinazolinone stereoisomers To a stirred solution of 1.86 g of 1-methyl-2-piperidone in 20 ml of tetrahydrofuran at −78° C. is added dropwise 16.36 ml of lithium bis(trimethylsilylamide)(1.0M in tetrahydrofuran) followed by stirring for 1.5 hours. To the reaction mixture is added portionwise 4.03 g of cerium chloride and is stirred at −78° C. for 1 hour. To the stirred mixture is added portionwise 1.0 g of 6-acetyl-2-butyl-4(1H)-quinazolinone and 40 ml of tetrahydrofuran. The mixture is stirred at −78° C. for 4 hours and then at 0° C. for 18 hours. The mixture is cooled to −78° C. and quenched with 30 ml of saturated ammonium chloride solution. After warming to room temperature, the mixture is filtered through diateomaceous earth and the filter cake washed with ethyl acetate. The filtrate is concentrated and extracted with ethyl acetate. The extract is washed with water, brine, dried (Na$_2$SO$_4$) and the solvent removed. The residue is purified by chromatography on silica gel with ethyl acetate-hexanes (1:1) as solvent and then ethyl acetate-methanol (1:1) as solvent to give 1.3 g of product as a yellow oil. Mass Spec MSFABL 358 (M+H).

EXAMPLE 50

2-Butyl-6-1-hydroxy-1-(1-methyl-2-oxo-3-piperidinyl)ethyl]-3-[[2'-[1-triphenylmethyl)-1H-tetrazol-5-yl][1,1'-biphenyl]-4-yl]methyl-4(3H)-quinazolinone isomer 1

EXAMPLE 51

2-Butyl-6-[1-hydroxy-1-(1-methyl-2-oxo-3-piperidinyl)ethyl]-3-[[2'-[1-triphenylmethyl)-1H-tetrazol-5-yl][1,1'-biphenyl]-4-yl]methyl-4(3H)-quinazolinone isomer 2

To a solution 1.1 g of 2-butyl-6-[1-hydroxy-(1-methyl-2-oxo-3-piperidinyl)ethyl]-4(1H)-quinazolinone (Example 49) in 12 ml of N,N-dimethylformamide is added 116.9 mg of lithium methoxide, followed by 3.43 g of 5-[4'-(bromomethyl)-[1,1'-biphenyl]-2-yl]-1-(triphenylmethyl)-1H-tetrazole. After stirring 10 minutes, 461.3 mg of sodium iodide is added and the mixture is heated at 50° C. overnight. The volatiles are removed under high vacuum and 120 ml of ethyl acetate added. The organic layer is separated and the aqueous layer extracted with ethyl acetate. The combined extracts are dried (Na$_2$SO$_4$) and the solvent removed. The residue is purified by chromatography (HPLC) on silica gel with ethyl acetate-hexanes (2:1) as solvent to give 332 mg of the less polar isomer (isomer 1) (Example 50) as a white foam and 253 mg of the more polar isomer 2 as a white foam. (Example 50) Mass Spec MSFABL 834 (M+H); (Example 51) Mass Spec MSFABL 834 (M+H).

EXAMPLE 52

2-Butyl-6-[1-hydroxy(1-methyl-2-oxo-3-piperidinyl)ethyl]-3-[[2'-(1H-tetrazol-5-yl)-[1,1'-biphenyl]-4-yl]methyl]-4(3H)-quinazolinone, isomer 1

As describe for Example 47, a solution of 280 mg of Example 50 (isomer 1) in 1 ml of tetrahydrofuran and 5 ml of methanol is refluxed overnight and the solvent removed. The residue is purified by chromatography on thick layer silica gel plates with ethyl acetate-methanol (2:1) as solvent to give 91 mg of product as a white foam. Mass Spec MSFABL 614 (M+Na).

EXAMPLE 53

2-Butyl-6-[1-hydroxy(1-methyl-2-oxo-3-piperidinyl)ethyl]-3-[[2'-(1H-tetrazol-5-yl)[1,1'-biphenyl]-4-yl]methyl]-4(3H)-quinazolinone isomer 2

As described for Example, 47, a solution o 630 mg of Example 51 (isomer 2) in 2 ml of tetrahydrofuran and 10 ml of methanol is refluxed overnight and the solvent removed. The residue is purified by chromatography on thick layer silica gel plates to give 235 mg of product as a white foam. Mass Spec MSFABL 614 (M+Na).

EXAMPLE 54

2-Butyl-6-[(hexahydro-1-methyl-2-oxo-1H-azepin-3-yl)hydroxymethyl]-3-[[2'-(1H-tetrazol-5-yl)[1,1'biphenyl]-4-yl]methyl-4-(3H)-quinazolinone isomer 1

EXAMPLE 55

2-Butyl-6-[(hexahydro-1-methyl-2-oxo-1H-azepin-3-yl)hydroxymethyl]-3-[[2'-(1H-tetrazol-5-yl)[1,1'-biphenyl]-4-yl]methyl-4(3H)quinazolinone isomer 2

To a solution of 6.7 ml of N-methyl caprolactam in 50 ml of tetrahydrofuran at −70° C. is added dropwise under argon 52.2 ml of lithium bis(trimethylsilyl)amide(1.0M in tetrahydrofuran) at −70° C. The mixture is stirred for 1.5 hour and then 3.0 g of 2-butyl-1,4-dihydro-4-oxo-6-quinazolinecarboxaldehyde is added portionwise. The mixture is diluted with 10 ml of tetrahydrofuran and stirred at −70° C. to −60° C. for 5 hours, allowed to warm to 0° C. and stand at 2° C. overnight. To the mixture is added 75 ml of saturated ammonium chloride and the mixture concentrated and then diluted with 30 ml of water. The mixture is extracted with two 300 ml portions of ethyl acetate. The extract is washed with 120 ml each of water, brine and dried ($Na_2SO_4$) The solvent is removed and the residue purified by high pressure chromatography (HPLC) on silica gel with 1% methanol in ethyl acetate as solvent to give 800 mg of a solid. The preceding solid (760 ml) is dissolved in 10 ml of N,N-dimethylformamide and then 80.73 mg of lithium methoxide added. To the reaction mixture is added 2.47 g of 5-[4'-(bromomethyl)[1,1'-biphenyl]-2-yl]-1-triphenylmethyl)-1H-tetrazole followed by 318.7 mg of sodium iodide. The mixture is heated at 55° C. overnight and the volatiles removed under high vacuum. The residue is diluted with 100 ml of ethyl acetate and washed with water and brine. The organic layer is dried ($Na_2SO_4$) and the solvent removed to give 3.5 g of solid. The solid is dissolved in ethyl acetate-hexanes (1:3) and the solution is filtered through a short column of silica gel to remove more polar material. The column is washed with ethyl acetate-methanol (1:2) and the solvent removed to give 1.0 g of solid. This solid is dissolved in 3 ml of tetrahydrofuran and 15 ml of methanol and the mixture refluxed overnight. The solvent is removed and the residue purified by chromatography (twice) on thick layer silica gel plates to give 117 mg of isomer 1 (Example 54) as a white foam (less polar compound) and 88 mg of the product (isomer 2) as a white foam. (Example 54) Mass Spec MSFABL 636 (M+Na); (Example 55) Mass Spec MSFABL 613 (M+Na).

EXAMPLE 56

2-Butyl-6-[1-hydroxy-1-(1-methyl-2-oxo-3-pyrrolidinyl)ethyl]-3-[[2'-[1H-(tetrazol-5-yl)-[1,1'-biphenyl]-4-yl]methyl-4(3H)-quinazoline, isomer 1, Sodium Salt A solution of 2-Butyl-6-[1-hydroxy-1-(1-methyl-2-oxo-3-pyrrolidinyl)ethyl]-3-[[2'-[1H-(tetrazol-5-yl)-[1,1'-biphenyl]-4-yl]methyl-4(3H)-quinazoline, isomer 1 (Example 47) and 1N sodium hydroxide in methyl alcohol is stirred at room temperature for one (1) hour. The volatiles are evaporated in vacuo to a solid which is dried to give 0.62 g of the desired product.

EXAMPLES 57-77

The procedure of Example 56 is substantially followed with the listed starting materials to obtain the desired salt product.

| Example | Starting Material of Example | Starting Base Material | Salt Product |
|---------|------------------------------|------------------------|--------------|
| 57 | 15 | Sodium Hydroxide | Sodium |
| 58 | 16 | Sodium Hydroxide | Sodium |
| 59 | 20 | Sodium Hydroxide | Sodium |
| 60 | 23 | Sodium Hydroxide | Sodium |
| 61 | 24 | Sodium Hydroxide | Sodium |
| 62 | 28 | Sodium Hydroxide | Sodium |
| 63 | 32 | Sodium Hydroxide | Sodium |
| 64 | 33 | Sodium Hydroxide | Sodium |
| 65 | 37 | Sodium Hydroxide | Sodium |
| 66 | 38 | Sodium Hydroxide | Sodium |
| 67 | 42 | Sodium Hydroxide | Sodium |
| 68 | 43 | Sodium Hydroxide | Sodium |
| 69 | 48 | Sodium Hydroxide | Sodium |
| 70 | 47 | Potassium Hydroxide | Potassium |
| 71 | 47 | Calcium Hydroxide | Calcium |
| 72 | 47 | Magnesium Hydroxide | Magnesium |
| 73 | 47 | Ammonium Hydroxide | Ammonium |
| 74 | 52 | Sodium Hydroxide | Sodium |
| 75 | 53 | Sodium Hydroxide | Sodium |
| 76 | 54 | Sodium Hydroxide | Sodium |
| 77 | 55 | Sodium Hydroxide | Sodium |

Angiotensin II Antagonists In Vitro Tests Materials and Methods:

Beef adrenals are obtained from a local slaughter house (Maxwell-Cohen). [$^{125}$I](Sar$^1$,Ile$^8$)AngII, S.A. 2200 Ci/mmole, is purchased from Dupont (NEN ®, Boston, Mass.). All unlabeled AngII analogs, Dimethylsulfoxide (DMSO), nucleotides, bovine serum albumin (BSA) are purchased from Sigma Chemical Co., St. Louis, Mo. U.S.A.

Preparation of Membranes:

Approximately sixteen (16) to twenty (20) beef adrenal glands are processed as follows: fresh adrenal glands received on crushed ice are cleaned of fatty tissues and the tough membranes encapsulating the glands are removed and discarded. The brownish tissue forming the adrenal cortex is scraped off and finely minced with scissors before homogenization. Care is taken to avoid contamination with medullary tissue during dissection. The scraped cortices are suspended in twenty volumes of an ice-cold buffer medium consisting of 10 mM Tris.HCl (pH 7.4 at 22° C.) and containing 1.0 mM EDTA and 0.2M sucrose. Unless otherwise indicated, all subsequent operations are done at 4° C. The tissue is homogenized in a glass homogenizer with a motor-driven teflon pestle with a clearance of 1.0 mm. The homogenate is centrifuged first at low speed (3,000×g) for 10 minutes. The resulting pellet is discarded and the supernatant fluid recentrifuged at 10,000×g for 15 minutes to give a P$_2$ pellet. This P$_2$ pellet is discarded and the liquid phase is carefully decanted off in clean centrifuge tubes and recentrifuged at high speed (100,000×g) for 60 minutes. The translucent final pellet is harvested and combined in a small volume (20–50.0 ml) of 50.0 mM Tris.HCl buffer, pH 7.2. A 100 ul aliquot is withdrawn and the protein content of the preparation is determined by the Lowry's method (Lowry, O. H., Rosebrough, N. F., Farr, A. L. and Randall, R. J., Protein measurement with Folin phenol reagent. J. Biol. Chem., 48, 265-275, 1951). The pelleted membrane is reconstituted in 50.0 mM Tris.HCl buffer containing 0.1 mM of phenylmethylsulfonyl fluoride (PMSF) to give approximately a protein concentration of 2.5 mg per ml of tissue suspension. The membrane preparation is finally aliquoted in 1.0 ml volumes and stored at $-70°$ C. until use in the binding assays.

Receptor Binding Assay: Binding of [$^{125}$I](Sar$^1$,Ile$^8$-)AngII

The binding of [$^{125}$I](Sar$^1$,Ile$^8$)AngII to microsomal membranes is initiated by the addition of reconstituted membranes (1:10 vols.) in freshly made 50.0 mM Tris.HCl buffer, pH 7.4 containing 0.25% heat inactivated bovine serum albumin (BSA): 80 ul membrane protein (10 to 20 ug/assay) to wells already containing 100 ul of incubation buffer (as described above) and 20 ul [$^{125}$I](Sar$^1$,Ile$^8$)AngII (Specific Activity, 2200 Ci/mmole). Non-specific binding is measured in the presence of 1.0 uM unlabeled (Sar$^1$,Ile$^8$)AngII, added in 20 ul volume. Specific binding for [$^{125}$I](Sar$^1$,Ile$^8$) AngII is greater than 90%. In competition studies, experimental compounds are diluted in dimethylsulfoxide (DMSO) and added in 20 ul to wells before the introduction of tissue membranes. This concentration of DMSO is found to have no negative effects on the binding of [$^{125}$I](Sar$^1$,Ile$^8$) AngII to the membranes. Assays are performed in triplicate. The wells are left undisturbed for 60 minutes at room temperature. Following incubation, all wells are harvested at once with a Brandel ® Harvester especially designed for a 96 well plate (Brandel ® Biomedical Research & Development Labs. Inc., Gaithersburg, Md., U.S.A.). The filter discs are washed with 10×1.0 ml of cold 0.9% NaCl to remove unbound ligand. Presoaking the filter sheet in 0.1% polyethyleneimine in normal saline (PEI/Saline) greatly reduces the radioactivity retained by the filter blanks. This method is routinely used. The filters are removed from the filter grid and counted in a Parkard ® Cobra Gamma Counter for 1 minutes. (Packard Instrument Co., Downers Grove, Ill, U.S.A.). The binding data are analyzed by the non-linear interactive "LUNDON-1" program (LUNDON SOFTWARE Inc., Cleveland, Ohio U.S.A.). Compounds that displace 50% of the labelled angiotensin II at the screening dose of 50 $\mu$M are considered active compounds and are then evaluated in concentration-response experiments to determine their IC$_{50}$ values. The results are shown in Table I.

TABLE I

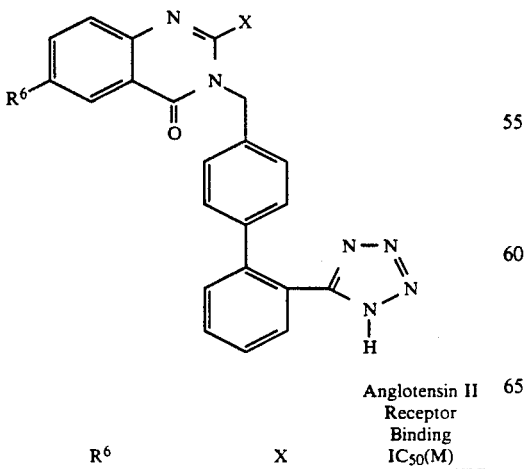

Angiotensin II Receptor Binding

| Ex. No. | R$^6$ | X | IC$_{50}$(M) |
|---|---|---|---|
| 15 | (2,2-dioxo-tetrahydrothiophene-3-ol) | $-(CH_2)_3CH_3$ | $11.0 \times 10^{-8}$ |
| 16 | (2,2-dioxo-tetrahydrothiophene-3-ol) | $-(CH_2)_3CH_3$ | $11.0 \times 10^{-8}$ |
| 23 | (3-methoxy-tetrahydrofuran) | $-(CH_2)_3CH_3$ | $6.8 \times 10^{-8}$ |
| 24 | (3-methoxy-tetrahydrofuran) | $-(CH_2)_3CH_3$ | $3.8 \times 10^{-8}$ |
| 28 | (2-hydroxyethyl-tetrahydrofuran) | $-(CH_2)_3CH_3$ | $13.0 \times 10^{-8}$ |
| 32 | (N-methyl-3-hydroxy-2-pyrrolidinone) | $-(CH_2)_3CH_3$ | $4.1 \times 10^{-8}$ |
| 33 | (N-methyl-3-hydroxy-2-pyrrolidinone) | $-(CH_2)_3CH_3$ | $2.9 \times 10^{-8}$ |
| 37 | (N-methyl-3-hydroxy-2-piperidinone) | $-(CH_2)_3CH_3$ | $4.1 \times 10^{-8}$ |
| 38 | (N-methyl-3-hydroxy-2-piperidinone) | $-(CH_2)_3CH_3$ | $6.7 \times 10^{-8}$ |
| 42 | (N-methyl-3-methoxy-2-piperidinone) | $-(CH_2)_3CH_3$ | $9.2 \times 10^{-8}$ |
| 43 | (N-methyl-3-methoxy-2-piperidinone) | $-(CH_2)_3CH_3$ | $7.1 \times 10^{-8}$ |

TABLE I-continued

| | | | |
|---|---|---|---|
| 47 | 3-(2-hydroxypropan-2-yl)-1-methylpyrrolidin-2-one | —(CH$_2$)$_3$CH$_3$ | 4.0 × 10$^{-8}$ |
| 48 | 3-(2-hydroxypropan-2-yl)-1-methylpyrrolidin-2-one | —(CH$_2$)$_3$CH$_3$ | 4.3 × 10$^{-8}$ |
| 52 | 3-(2-hydroxypropan-2-yl)-1-methylpyrrolidin-2-one | —(CH$_2$)$_3$CH$_3$ | 6.2 × 10$^{-8}$ |
| 53 | 3-(2-hydroxypropan-2-yl)-1-methylpyrrolidin-2-one | —(CH$_2$)$_3$CH$_3$ | 5.4 × 10$^{-8}$ |
| 54 | 3-(1-hydroxyethyl)-1-methylazepan-2-one | —(CH$_2$)$_3$CH$_3$ | 4.3 × 10$^{-7}$ |
| 55 | 3-(1-hydroxyethyl)-1-methylazepan-2-one | —(CH$_2$)$_3$CH$_3$ | 1.5 × 10$^{-7}$ |

The compounds of this invention inhibit the action of AII. By administering a compound of this invention to a rat, and then challenging with angiotensin II, a blockage of the vasopressor response is realized. The results of this test on representative compounds of this invention are shown in Table II.

AII Challenge

Conscious Male Okamoto-Aoki SHR, 16–20 weeks old, weighing approximately 330 g are purchased from Charles River Labs (Wilmington, Mass.). Conscious rats are restrained in a supine position with elastic tape. The area at the base of the tail is locally anesthetized by subcutaneous infiltration with 2% procaine. The ventral caudal artery and vein are isolated, and a cannula made of polyethylene (PE) 10-20 tubing (fused together by heat) is passed into the lower abdominal aorta and vena cava, respectively. The cannula is secured, heparinized (1,000 I.U./ml), sealed and the wound is closed. The animals are placed in plastic restraining cages in an upright position. The cannula is attached to a Statham P23Db pressure transducer, and pulsatile blood pressure is recorded to 10-15 minutes with a Gould Brush recorder. (Chan et al., (Drug Development Res., 18:75-94, 1989).

Angiotensin II (human sequence, Sigma Chem. Co., St. Louis, MO) of 0.05 and 0.1 ug/kg i.v. is injected into all rats (predosing response). Then a test compound, vehicle or a known angiotensin II antagonist is administered i.v., i.p. or orally to each set of rats. The two doses of angiotensin II are given to each rat again at 30, 60, 90, 120, 180, 240 and 300 minutes post dosing the compound or vehicle. The vasopressor response of angiotensin II is measured for the increase in systolic blood pressure in mmHg. The percentage of antagonism or blockade of the vasopressor response of angiotensin II by a compound is calculated using the vasopressor response (increase in systolic blood pressure) of angiotensin II of each rat predosing the compound as 100%. A compound is considered active if at 30 mg/kg i.v. it antagonized at least 50% of the response.

TABLE II

ANGIOTENSIN II (AII) VASOPRESSOR RESPONSE

| Ex. No. | Dose (mg/kg) | AII Dose mcg/kg IV | Min Post Dose | Control Before AII | Response After AII | Change | Average Change | % Inhibition |
|---|---|---|---|---|---|---|---|---|
| CONTROL | | 0.05 | 0 | 200 | 249 | 49 | 40.5 | |
| | | | | 205 | 237 | 32 | | |
| | | 0.1 | | 195 | 250 | 55 | 50 | |
| | | | | 195 | 240 | 45 | | |
| 15 | 3 i.v. | 0.05 | 30 | 195 | 200 | 5 | 5 | 88 |
| | | | | 195 | 200 | 5 | | |
| | | 0.01 | | 185 | 200 | 15 | 12.5 | 75 |
| | | | | 190 | 200 | 10 | | |
| | | 0.05 | 60 | 193 | 210 | 17 | 11 | 73 |
| | | | | 195 | 200 | 5 | | |
| | | 0.1 | | 190 | 207 | 17 | 18.5 | 63 |
| | | | | 185 | 205 | 20 | | |
| | | 0.05 | 90 | 195 | 202 | 7 | 7 | 83 |
| | | | | 198 | 205 | 7 | | |
| | | 0.1 | | 190 | 215 | 25 | 23 | 54 |
| | | | | 192 | 213 | 21 | | |
| | | 0.05 | 120 | 185 | 215 | 30 | 27.5 | 32 |
| | | | | 185 | 210 | 25 | | |
| | | 0.1 | | 190 | 220 | 30 | 27.5 | 45 |

TABLE II-continued

ANGIOTENSIN II (AII) VASOPRESSOR RESPONSE

| Ex. No. | Dose (mg/kg) | AII Dose mcg/kg IV | Min Post Dose | Control Before AII | Response After AII | Change | Average Change | % Inhibition |
|---|---|---|---|---|---|---|---|---|
| | | | | 185 | 210 | 25 | | |
| | | 0.05 | 180 | 185 | 207 | 22 | 23.5 | 42 |
| | | | | 185 | 210 | 25 | | |
| | | 0.1 | | 185 | 225 | 40 | 25 | 50 |
| | | | | 185 | 195 | 10 | | |
| | | 0.05 | 240 | 190 | 235 | 45 | 25 | 38 |
| | | | | 190 | 195 | 5 | | |
| | | 0.1 | | 205 | 250 | 45 | 25 | 50 |
| | | | | 185 | 190 | 5 | | |
| | | 0.05 | 300 | 190 | 240 | 50 | 30 | 26 |
| | | | | 185 | 195 | 10 | | |
| | | 0.1 | | 200 | 225 | 25 | 27.5 | 45 |
| | | | | 185 | 215 | 30 | | |
| SPONTANEOUSLY HYPERTENSIVE RATS n = 2 Body weight(s): 310,270 grams | | | | | | | | |
| CONTROL | | 0.05 | 0 | 165 | 220 | 55 | 45 | |
| | | | | 155 | 190 | 35 | | |
| | | 0.1 | | 180 | 225 | 45 | 35 | |
| | | | | 180 | 205 | 25 | | |
| 16 | 3 i.v. | 0.05 | 30 | 165 | 175 | 10 | 12.5 | 72 |
| | | | | 185 | 200 | 15 | | |
| | | 0.1 | | 165 | 175 | 10 | 20 | 43 |
| | | | | 175 | 205 | 30 | | |
| | | 0.05 | 60 | 170 | 185 | 15 | 31.5 | 30 |
| | | | | 160 | 208 | 48 | | |
| | | 0.1 | | 175 | 185 | 10 | 12.5 | 64 |
| | | | | 165 | 180 | 15 | | |
| | | 0.05 | 90 | 160 | 180 | 20 | 17.5 | 61 |
| | | | | 160 | 175 | 15 | | |
| | | 0.1 | | 160 | 185 | 25 | 22.5 | 36 |
| | | | | 160 | 180 | 20 | | |
| | | 0.05 | 120 | 170 | 180 | 10 | 13 | 71 |
| | | | | 164 | 180 | 16 | | |
| | | 0.1 | | 175 | 190 | 15 | 17.5 | 50 |
| | | | | 165 | 185 | 20 | | |
| | | 0.05 | 180 | 160 | 180 | 20 | 27.5 | 39 |
| | | | | 155 | 190 | 35 | | |
| | | 0.1 | | 160 | 190 | 30 | 30 | 14 |
| | | | | 170 | 200 | 30 | | |
| | | 0.05 | 240 | 160 | 185 | 25 | 27.5 | 39 |
| | | | | 165 | 195 | 30 | | |
| | | 0.1 | | 160 | 200 | 40 | 35 | 0 |
| | | | | 175 | 205 | 30 | | |
| | | 0.05 | 300 | 165 | 200 | 35 | 30 | 33 |
| | | | | 165 | 190 | 25 | | |
| | | 0.1 | | 165 | 210 | 45 | 42.5 | −21 |
| | | | | 160 | 200 | 40 | | |
| SPONTANEOUSLY HYPERTENSIVE RATS n = 2 Body weight(s): 310,300 grams | | | | | | | | |
| CONTROL | | 0.05 | 0 | 250 | 290 | 40 | 35 | |
| | | | | 215 | 245 | 30 | | |
| | | 0.1 | | 260 | 300 | 40 | 40 | |
| | | | | 220 | 260 | 40 | | |
| 23 | 3 i.v. | 0.05 | 30 | 245 | 247 | 2 | 1 | 97 |
| | | | | 245 | 245 | 0 | | |
| | | 0.1 | | 247 | 250 | 3 | 1.5 | 96 |
| | | | | 215 | 215 | 0 | | |
| | | 0.05 | 60 | 240 | 245 | 5 | 2.5 | 93 |
| | | | | 215 | 215 | 0 | | |
| | | 0.1 | | 245 | 250 | 5 | 6.5 | 84 |
| | | | | 205 | 213 | 8 | | |
| | | 0.05 | 90 | 245 | 250 | 5 | 7.5 | 79 |
| | | | | 215 | 225 | 10 | | |
| | | 0.1 | | 240 | 252 | 12 | 8.5 | 79 |
| | | | | 210 | 215 | 5 | | |
| | | 0.05 | 120 | 210 | 215 | 5 | 7.5 | 79 |
| | | | | 215 | 225 | 10 | | |
| | | 0.1 | | 230 | 240 | 10 | 7.5 | 81 |
| | | | | 220 | 225 | 5 | | |
| | | 0.05 | 180 | 240 | 245 | 5 | 7.5 | 79 |
| | | | | 215 | 225 | 10 | | |
| | | 0.1 | | 240 | 245 | 5 | 10 | 75 |
| | | | | 210 | 225 | 15 | | |
| | | 0.05 | 240 | 195 | 210 | 15 | 14 | 60 |
| | | | | 175 | 188 | 13 | | |
| | | 0.1 | | 190 | 215 | 25 | 20 | 50 |
| | | | | 175 | 190 | 15 | | |
| | | 0.05 | 300 | 230 | 245 | 15 | 17.5 | 50 |
| | | | | 200 | 220 | 20 | | |
| | | 0.1 | | 230 | 260 | 30 | 20 | 50 |
| | | | | 215 | 225 | 10 | | |

TABLE II-continued

| | | ANGIOTENSIN II (AII) VASOPRESSOR RESPONSE | | | | | | |
|---|---|---|---|---|---|---|---|---|
| Ex. No. | Dose (mg/kg) | AII Dose mcg/kg IV | Min Post Dose | Control Before AII | Response After AII | Change | Average Change | % Inhibition |
| SPONTANEOUSLY HYPERTENSIVE RATS n = 2 Body weight(s): 290,280 grams | | | | | | | | |
| CONTROL | | 0.05 | 0 | 220 | 260 | 40 | 47.5 | |
| | | | | 225 | 280 | 55 | | |
| | | 0.1 | | 215 | 265 | 50 | 55 | |
| | | | | 220 | 280 | 60 | | |
| 23 | 3 p.o. | 0.05 | 30 | 220 | 235 | 15 | 20 | 58 |
| | | | | 225 | 250 | 25 | | |
| | | 0.1 | | 205 | 245 | 40 | 45 | 18 |
| | | | | 215 | 265 | 50 | | |
| | | 0.05 | 60 | 220 | 245 | 25 | 37.5 | 21 |
| | | | | 215 | 265 | 50 | | |
| | | 0.1 | | 220 | 265 | 45 | 47.5 | 14 |
| | | | | 215 | 265 | 50 | | |
| | | 0.05 | 90 | 230 | 250 | 20 | 30 | 37 |
| | | | | 220 | 260 | 40 | | |
| | | 0.1 | | 225 | 255 | 30 | 37.5 | 32 |
| | | | | 220 | 265 | 45 | | |
| | | 0.05 | 120 | 225 | 245 | 20 | 25 | 47 |
| | | | | 215 | 245 | 30 | | |
| | | 0.1 | | 220 | 255 | 35 | 35 | 36 |
| | | | | 225 | 260 | 35 | | |
| | | 0.05 | 180 | 225 | 245 | 20 | 37.5 | 21 |
| | | | | 205 | 260 | 55 | | |
| | | 0.1 | | 215 | 270 | 55 | 9 | |
| | | | | 220 | 265 | 45 | | |
| SPONTANEOUSLY HYPERTENSIVE RATS n = 2 Body weight(s): 370,360 grams | | | | | | | | |
| CONTROL | | 0.05 | 0 | 225 | 265 | 40 | 37.5 | |
| | | | | 220 | 255 | 35 | | |
| | | 0.1 | | 230 | 268 | 38 | 39 | — |
| | | | | 230 | 270 | 40 | | |
| 24 | 3 i.v. | 0.05 | 30 | 210 | 210 | 0 | 0 | 100 |
| | | | | 230 | 230 | 0 | | |
| | | 0.1 | | 210 | 210 | 0 | 0 | 100 |
| | | | | 230 | 230 | 0 | | |
| | | 0.05 | 60 | 210 | 212 | 2 | 2.5 | 93 |
| | | | | 230 | 233 | 3 | | |
| | | 0.1 | | 205 | 210 | 5 | 5 | 87 |
| | | | | 225 | 230 | 5 | | |
| | | 0.05 | 90 | 210 | 215 | 5 | 2.5 | 93 |
| | | | | 220 | 220 | 0 | | |
| | | 0.1 | | 215 | 220 | 5 | 5 | 87 |
| | | | | 215 | 220 | 5 | | |
| | | 0.05 | 120 | 215 | 225 | 10 | 5 | 87 |
| | | | | 230 | 230 | 0 | | |
| | | 0.1 | | 210 | 210 | 0 | 0 | 100 |
| | | | | 220 | 220 | 0 | | |
| | | 0.05 | 180 | 200 | 215 | 15 | 7.5 | 80 |
| | | | | 220 | 220 | 0 | | |
| | | 0.1 | | 195 | 195 | 0 | 7.5 | 81 |
| | | | | 220 | 235 | 15 | | |
| | | 0.05 | 240 | 190 | 195 | 5 | 7.5 | 80 |
| | | | | 220 | 230 | 10 | | |
| | | 0.1 | | 190 | 200 | 10 | 15 | 62 |
| | | | | 215 | 235 | 20 | | |
| | | 0.05 | 300 | 190 | 196 | 6 | 6.5 | 83 |
| | | | | 215 | 222 | 7 | | |
| | | 0.1 | | 220 | 232 | 12 | 16 | 59 |
| | | | | 215 | 235 | 20 | | |
| SPONTANEOUSLY HYPERTENSIVE RATS n = 2 Body weight(s): 280,300 grams | | | | | | | | |
| CONTROL | | 0.05 | 0 | 205 | 257 | 52 | 48.5 | |
| | | | | 215 | 260 | 45 | | |
| | | 0.1 | | 210 | 260 | 50 | 52.5 | |
| | | | | 215 | 270 | 55 | | |
| 24 | 3 p.o. | 0.05 | 30 | 205 | 230 | 25 | 17.5 | 64 |
| | | | | 205 | 215 | 10 | | |
| | | 0.1 | | 200 | 230 | 30 | 22.5 | 57 |
| | | | | 205 | 220 | 15 | | |
| | | 0.05 | 60 | 195 | 220 | 25 | 22.5 | 54 |
| | | | | 205 | 225 | 20 | | |
| | | 0.1 | | 195 | 230 | 35 | 32.5 | 38 |
| | | | | 205 | 235 | 30 | | |
| | | 0.05 | 90 | 195 | 225 | 30 | 25 | 48 |
| | | | | 210 | 230 | 20 | | |
| | | 0.1 | | 195 | 235 | 40 | 35 | 33 |
| | | | | 210 | 240 | 30 | | |
| | | 0.05 | 120 | 185 | 210 | 25 | 22.5 | 54 |
| | | | | 220 | 240 | 20 | | |
| | | 0.1 | | 195 | 230 | 35 | 37.5 | 29 |
| | | | | 210 | 250 | 40 | | |

TABLE II-continued

| | | ANGIOTENSIN II (AII) VASOPRESSOR RESPONSE | | | | | | |
|---|---|---|---|---|---|---|---|---|
| Ex. No. | Dose (mg/kg) | AII Dose mcg/kg IV | Min Post Dose | Control Before AII | Response After AII | Change | Average Change | % Inhibition |
| | | 0.05 | 180 | 195 | 240 | 45 | 39 | 20 |
| | | | | 215 | 248 | 33 | | |
| | | 0.1 | | 200 | 245 | 45 | 37.5 | 29 |
| | | | | 230 | 260 | 30 | | |
| | | 0.05 | 240 | 185 | 230 | 45 | 42.5 | 12 |
| | | | | 210 | 250 | 40 | | |
| | | 0.1 | | 195 | 240 | 45 | 40 | 24 |
| | | | | 215 | 250 | 35 | | |
| SPONTANEOUSLY HYPERTENSIVE RATS n = 2 Body weight(s): 310,320 grams | | | | | | | | |
| CONTROL | | 0.05 | 0 | 210 | 250 | 40 | 32.5 | |
| | | | | 220 | 245 | 25 | | |
| | | 0.1 | | 205 | 255 | 50 | 37.5 | |
| | | | | 220 | 245 | 25 | | |
| 32 | 3 p.o. | 0.05 | 30 | 205 | 245 | 40 | 32.5 | 0 |
| | | | | 210 | 235 | 25 | | |
| | | 0.1 | | 210 | 245 | 35 | 27.5 | 27 |
| | | | | 210 | 230 | 20 | | |
| | | 0.05 | 60 | 205 | 230 | 25 | 17.5 | 46 |
| | | | | 215 | 225 | 10 | | |
| | | 0.1 | | 215 | 245 | 30 | 27.5 | 27 |
| | | | | 210 | 235 | 25 | | |
| | | 0.05 | 90 | 210 | 230 | 20 | 12.5 | 62 |
| | | | | 215 | 220 | 5 | | |
| | | 0.1 | | 215 | 245 | 30 | 22.5 | 40 |
| | | | | 205 | 220 | 15 | | |
| | | 0.05 | 120 | 210 | 235 | 25 | 17.5 | 46 |
| | | | | 210 | 220 | 10 | | |
| | | 0.1 | | 205 | 244 | 39 | 27 | 28 |
| | | | | 210 | 225 | 15 | | |
| | | 0.05 | 180 | 205 | 228 | 23 | 29 | 11 |
| | | | | 200 | 235 | 35 | | |
| | | 0.1 | | 210 | 255 | 45 | 32.5 | 13 |
| | | | | 205 | 225 | 20 | | |
| | | 0.05 | 240 | 200 | 225 | 25 | 22.5 | 31 |
| | | | | 210 | 230 | 20 | | |
| | | 0.1 | | 205 | 250 | 45 | 29 | 23 |
| | | | | 207 | 220 | 13 | | |
| SPONTANEOUSLY HYPERTENSIVE RATS n = 2 Body weight(s): 315,280 grams | | | | | | | | |
| SPONTANEOUSLY HYPERTENSIVE RATS n = 2 Body weight(s): 310,280 grams | | | | | | | | |
| CONTROL | | 0.05 | 0 | 235 | 257 | 22 | 23.5 | |
| | | | | 220 | 245 | 25 | | |
| | | 0.1 | | 230 | 265 | 35 | 42.5 | |
| | | | | 210 | 260 | 50 | | |
| 32 | 3 i.v. | 0.05 | 30 | 220 | 220 | 0 | 0 | 100 |
| | | | | 210 | 210 | 0 | | |
| | | 0.1 | | 215 | 215 | 0 | 0 | 100 |
| | | | | 205 | 205 | 0 | | |
| | | 0.05 | 60 | 220 | 220 | 0 | 2.5 | 89 |
| | | | | 195 | 200 | 5 | | |
| | | 0.1 | | 220 | 220 | 0 | 1.5 | 96 |
| | | | | 200 | 203 | 3 | | |
| | | 0.05 | 90 | 215 | 215 | 0 | 2.5 | 89 |
| | | | | 190 | 195 | 5 | | |
| | | 0.1 | | 220 | 220 | 0 | 5 | 88 |
| | | | | 200 | 210 | 10 | | |
| | | 0.05 | 120 | 215 | 215 | 0 | 2.5 | 89 |
| | | | | 190 | 195 | 5 | | |
| | | 0.1 | | 205 | 210 | 5 | 2.5 | 94 |
| | | | | 215 | 215 | 0 | | |
| | | 0.05 | 180 | 215 | 225 | 10 | 7.5 | 68 |
| | | | | 190 | 195 | 5 | | |
| | | 0.1 | | 210 | 225 | 15 | 20 | 53 |
| | | | | 185 | 210 | 25 | | |
| | | 0.05 | 240 | 220 | 235 | 15 | 17.5 | 26 |
| | | | | 190 | 210 | 20 | | |
| | | 0.1 | | 210 | 235 | 25 | 32.5 | 24 |
| | | | | 195 | 235 | 40 | | |
| | | 0.05 | 300 | 220 | 253 | 33 | 26.5 | −13 |
| | | | | 190 | 210 | 20 | | |
| | | 0.1 | | 215 | 255 | 40 | 42.5 | 0 |
| | | | | 190 | 235 | 45 | | |
| SPONTANEOUSLY HYPERTENSIVE RATS n = 2 Body weight(s): 310,280 grams | | | | | | | | |
| CONTROL | | 0.05 | 0 | 210 | 260 | 50 | 50 | |
| | | | | 215 | 265 | 50 | | |
| | | 0.1 | | 210 | 260 | 50 | 47.5 | |
| | | | | 225 | 270 | 45 | | |
| 33 | 3 p.o. | 0.05 | 30 | 215 | 230 | 15 | 10 | 80 |
| | | | | 205 | 210 | 5 | | |
| | | 0.1 | | 210 | 245 | 35 | 17.5 | 63 |

TABLE II-continued

ANGIOTENSIN II (AII) VASOPRESSOR RESPONSE

| Ex. No. | Dose (mg/kg) | AII Dose mcg/kg IV | Min Post Dose | Control Before AII | Response After AII | Change | Average Change | % Inhibition |
|---|---|---|---|---|---|---|---|---|
| | | | | 210 | 210 | 0 | | |
| | | 0.05 | 60 | 210 | 240 | 30 | 17.5 | 65 |
| | | | | 210 | 215 | 5 | | |
| | | 0.1 | | 210 | 245 | 35 | 25 | 47 |
| | | | | 205 | 220 | 15 | | |
| | | 0.05 | 90 | 205 | 250 | 45 | 25 | 50 |
| | | | | 210 | 215 | 5 | | |
| | | 0.1 | | 220 | 260 | 40 | 30 | 37 |
| | | | | 200 | 220 | 20 | | |
| | | 0.05 | 120 | 210 | 237 | 27 | 18.5 | 63 |
| | | | | 205 | 215 | 10 | | |
| | | 0.1 | | 220 | 260 | 40 | 22.5 | 53 |
| | | | | 210 | 215 | 5 | | |
| | | 0.05 | 180 | 200 | 250 | 50 | 32.5 | 35 |
| | | | | 210 | 225 | 15 | | |
| | | 0.1 | | 210 | 270 | 60 | 37.5 | 21 |
| | | | | 210 | 225 | 15 | | |
| | | 0.05 | 240 | 205 | 235 | 30 | 35 | 30 |
| | | | | 205 | 245 | 40 | | |
| | | 0.1 | | 210 | 270 | 60 | 47.5 | 0 |
| | | | | 215 | 250 | 35 | | |
| SPONTANEOUSLY HYPERTENSIVE RATS n = 2 Body weight(s): 300,320 grams | | | | | | | | |
| CONTROL | | 0.05 | 0 | 220 | 260 | 40 | 40 | |
| | | | | 220 | 260 | 40 | | |
| | | 0.1 | | 220 | 270 | 50 | 52.5 | |
| | | | | 215 | 270 | 55 | | |
| 33 | 3 i.v. | 0.05 | 30 | 200 | 200 | 0 | 0 | 100 |
| | | | | 220 | 220 | 0 | | |
| | | 0.1 | | 195 | 200 | 5 | 7.5 | 86 |
| | | | | 210 | 220 | 10 | | |
| | | 0.05 | 60 | 210 | 210 | 0 | 0 | 100 |
| | | | | 205 | 205 | 0 | | |
| | | 0.1 | | 195 | 200 | 5 | 6 | 89 |
| | | | | 205 | 212 | 7 | | |
| | | 0.05 | 90 | 200 | 200 | 0 | 0 | 100 |
| | | | | 215 | 215 | 0 | | |
| | | 0.1 | | 190 | 195 | 5 | 7.5 | |
| | | | | 210 | 220 | 10 | | |
| | | 0.05 | 120 | 205 | 205 | 0 | 0 | 100 |
| | | | | 205 | 205 | 0 | | |
| | | 0.1 | | 205 | 220 | 15 | 10 | 81 |
| | | | | 210 | 215 | 5 | | |
| | | 0.05 | 180 | 210 | 215 | 5 | 7.5 | 81 |
| | | | | 195 | 205 | 10 | | |
| | | 0.1 | | 200 | 225 | 25 | 25 | 52 |
| | | | | 195 | 220 | 25 | | |
| | | 0.05 | 240 | 220 | 235 | 15 | 17.5 | 56 |
| | | | | 200 | 220 | 20 | | |
| | | 0.1 | | 200 | 240 | 40 | 35 | 33 |
| | | | | 205 | 235 | 30 | | |
| | | 0.05 | 300 | 240 | 255 | 15 | 22.5 | 44 |
| | | | | 205 | 235 | 30 | | |
| | | 0.1 | | 235 | 255 | 20 | 32.5 | 38 |
| | | | | 200 | 245 | 45 | | |
| SPONTANEOUSLY HYPERTENSIVE RATS n = 2 Body weight(s): 290,300 grams | | | | | | | | |
| CONTROL | | 0.05 | 0 | 210 | 260 | 50 | 52.5 | |
| | | | | 205 | 260 | 55 | | |
| | | 0.1 | | 215 | 260 | 45 | 50 | |
| | | | | 210 | 265 | 55 | | |
| 37 | 10 p.o. | 0.05 | 30 | 210 | 235 | 25 | 17.5 | 67 |
| | | | | 215 | 225 | 10 | | |
| | | 0.1 | | 210 | 245 | 35 | 30 | 40 |
| | | | | 215 | 240 | 25 | | |
| | | 0.05 | 60 | 205 | 225 | 20 | 18.5 | 65 |
| | | | | 210 | 227 | 17 | | |
| | | 0.1 | | 210 | 244 | 34 | 37 | 26 |
| | | | | 200 | 240 | 40 | | |
| | | 0.05 | 90 | 210 | 230 | 20 | 20 | 62 |
| | | | | 205 | 225 | 20 | | |
| | | 0.1 | | 210 | 240 | 30 | 30 | 40 |
| | | | | 210 | 240 | 30 | | |
| | | 0.05 | 120 | 210 | 230 | 20 | 17.5 | 67 |
| | | | | 210 | 225 | 15 | | |
| | | 0.1 | | 220 | 250 | 30 | 22.5 | 55 |
| | | | | 225 | 240 | 15 | | |
| | | 0.05 | 180 | 220 | 245 | 25 | 22.5 | 57 |
| | | | | 210 | 230 | 20 | | |
| | | 0.1 | | 210 | 245 | 35 | 32.5 | 35 |
| | | | | 210 | 240 | 30 | | |

TABLE II-continued

ANGIOTENSIN II (AII) VASOPRESSOR RESPONSE

| Ex. No. | Dose (mg/kg) | AII Dose mcg/kg IV | Min Post Dose | Control Before AII | Response After AII | Change | Average Change | % Inhibition |
|---|---|---|---|---|---|---|---|---|
| | | 0.05 | 240 | 200 | 240 | 40 | 30 | 43 |
| | | | | 210 | 230 | 20 | | |
| | | 0.1 | | 210 | 255 | 45 | 30 | 40 |
| | | | | 200 | 215 | 15 | | |
| | | 0.05 | 300 | 195 | 230 | 35 | 25 | 52 |
| | | | | 200 | 215 | 15 | | |
| | | 0.1 | | 200 | 240 | 40 | 32.5 | 35 |
| | | | | 200 | 225 | 25 | | |

SPONTANEOUSLY HYPERTENSIVE RATS n = 2 Body weight(s): 340,345 grams

| Ex. No. | Dose (mg/kg) | AII Dose mcg/kg IV | Min Post Dose | Control Before AII | Response After AII | Change | Average Change | % Inhibition |
|---|---|---|---|---|---|---|---|---|
| CONTROL | | 0.05 | 0 | 215 | 265 | 50 | 40 | |
| | | | | 215 | 245 | 30 | | |
| | | 0.1 | | 215 | 265 | 50 | 45 | |
| | | | | 215 | 255 | 40 | | |
| 37 | 3 p.o. | 0.05 | 30 | 220 | 230 | 10 | 19 | 53 |
| | | | | 205 | 233 | 28 | | |
| | | 0.1 | | 200 | 255 | 55 | 47.5 | −6 |
| | | | | 215 | 255 | 40 | | |
| | | 0.05 | 60 | 200 | 230 | 30 | 28.5 | 29 |
| | | | | 215 | 242 | 27 | | |
| | | 0.1 | | 207 | 240 | 33 | 31.5 | 30 |
| | | | | 215 | 245 | 30 | | |
| | | 0.05 | 90 | 200 | 230 | 30 | 28.5 | 29 |
| | | | | 210 | 237 | 27 | | |
| | | 0.1 | | 200 | 240 | 40 | 40 | 11 |
| | | | | 210 | 250 | 40 | | |
| | | 0.05 | 120 | 210 | 235 | 25 | 35 | 13 |
| | | | | 210 | 255 | 45 | | |
| | | 0.1 | | 220 | 260 | 40 | 35 | 22 |
| | | | | 230 | 260 | 30 | | |
| | | 0.05 | 180 | 200 | 230 | 30 | 40 | 0 |
| | | | | 210 | 260 | 50 | | |
| | | 0.1 | | 205 | 240 | 35 | 35 | 22 |
| | | | | 230 | 265 | 35 | | |

SPONTANEOUSLY HYPERTENSIVE RATS n = 2 Body weight(s): 350,360 grams

| Ex. No. | Dose (mg/kg) | AII Dose mcg/kg IV | Min Post Dose | Control Before AII | Response After AII | Change | Average Change | % Inhibition |
|---|---|---|---|---|---|---|---|---|
| CONTROL | | 0.05 | 0 | 215 | 265 | 50 | 40 | |
| | | | | 215 | 245 | 30 | | |
| | | 0.1 | | 215 | 265 | 50 | 45 | |
| | | | | 215 | 255 | 40 | | |
| 37 | 3 p.o. | 0.05 | 30 | 220 | 230 | 10 | 19 | 53 |
| | | | | 205 | 233 | 28 | | |
| | | 0.1 | | 200 | 255 | 55 | 47.5 | −6 |
| | | | | 215 | 255 | 40 | | |
| | | 0.05 | 60 | 200 | 230 | 30 | 28.5 | 29 |
| | | | | 215 | 242 | 27 | | |
| | | 0.1 | | 207 | 240 | 33 | 31.5 | 30 |
| | | | | 215 | 245 | 30 | | |
| | | 0.05 | 90 | 200 | 230 | 30 | 28.5 | 29 |
| | | | | 210 | 237 | 27 | | |
| | | 0.1 | | 200 | 240 | 40 | 40 | 11 |
| | | | | 210 | 250 | 40 | | |
| | | 0.05 | 120 | 210 | 235 | 25 | 35 | 13 |
| | | | | 210 | 255 | 45 | | |
| | | 0.1 | | 220 | 260 | 40 | 35 | 22 |
| | | | | 230 | 260 | 30 | | |
| | | 0.05 | 180 | 200 | 230 | 30 | 40 | 0 |
| | | | | 210 | 260 | 50 | | |
| | | 0.1 | | 205 | 240 | 35 | 35 | 22 |
| | | | | 230 | 265 | 35 | | |

SPONTANEOUSLY HYPERTENSIVE RATS n = 2 Body weight(s): 350,360 grams

| Ex. No. | Dose (mg/kg) | AII Dose mcg/kg IV | Min Post Dose | Control Before AII | Response After AII | Change | Average Change | % Inhibition |
|---|---|---|---|---|---|---|---|---|
| CONTROL | | 0.05 | 0 | 235 | 255 | 20 | 27.5 | |
| | | | | 240 | 275 | 35 | | |
| | | 0.1 | | 230 | 260 | 30 | 32.5 | |
| | | | | 245 | 280 | 35 | | |
| 37 | 3 i.v. | 0.05 | 30 | 220 | 220 | 0 | 0 | 100 |
| | | | | 230 | 230 | 0 | | |
| | | 0.1 | | 220 | 225 | 5 | 2.5 | 92 |
| | | | | 230 | 230 | 0 | | |
| | | 0.05 | 60 | 240 | 240 | 0 | 0 | 100 |
| | | | | 245 | 245 | 0 | | |
| | | 0.1 | | 245 | 250 | 5 | 2.5 | 92 |
| | | | | 245 | 245 | 0 | | |
| | | 0.05 | 90 | 250 | 250 | 0 | 0 | 100 |
| | | | | 235 | 235 | 0 | | |
| | | 0.1 | | 250 | 255 | 5 | 5 | 85 |
| | | | | 185 | 190 | 5 | | |
| | | 0.05 | 120 | 260 | 265 | 5 | 2.5 | 91 |
| | | | | 225 | 225 | 0 | | |
| | | 0.1 | | 250 | 260 | 10 | 5 | 85 |
| | | | | 225 | 225 | 0 | | |

TABLE II-continued

| | | ANGIOTENSIN II (AII) VASOPRESSOR RESPONSE | | | | | | |
|---|---|---|---|---|---|---|---|---|
| Ex. No. | Dose (mg/kg) | AII Dose mcg/kg IV | Min Post Dose | Control Before AII | Response After AII | Change | Average Change | % Inhibition |
| | | 0.05 | 180 | 240 | 250 | 10 | 12.5 | 55 |
| | | | | 230 | 245 | 15 | | |
| | | 0.1 | | 245 | 265 | 20 | 11 | 66 |
| | | | | 233 | 235 | 2 | | |
| | | 0.05 | 240 | 235 | 255 | 20 | 10 | 64 |
| | | | | 230 | 230 | 0 | | |
| | | 0.1 | | 230 | 260 | 30 | 25 | 23 |
| | | | | 235 | 255 | 20 | | |
| | | 0.05 | 300 | 245 | 270 | 25 | 17.5 | 36 |
| | | | | 230 | 240 | 10 | | |
| | | 0.1 | | 250 | 285 | 35 | 32.5 | 0 |
| | | | | 235 | 265 | 30 | | |
| SPONTANEOUSLY HYPERTENSIVE RATS n = 2 Body weight(s): 300,300 grams | | | | | | | | |
| CONTROL | | 0.05 | 0 | 205 | 255 | 50 | 50 | |
| | | | | 225 | 275 | 50 | | |
| | | 0.1 | | 210 | 260 | 50 | 57.5 | |
| | | | | 220 | 285 | 65 | | |
| 38 | 10 p.o. | 0.05 | 30 | 205 | 230 | 25 | 25 | 50 |
| | | | | 220 | 245 | 25 | | |
| | | 0.1 | | 210 | 240 | 30 | 37.5 | 35 |
| | | | | 220 | 265 | 45 | | |
| | | 0.05 | 60 | 215 | 235 | 20 | 30 | 40 |
| | | | | 220 | 260 | 40 | | |
| | | 0.1 | | 210 | 245 | 35 | 35 | 39 |
| | | | | 235 | 270 | 35 | | |
| | | 0.05 | 90 | 210 | 245 | 35 | 37.5 | 25 |
| | | | | 230 | 270 | 40 | | |
| | | 0.1 | | 220 | 250 | 30 | 37.5 | 35 |
| | | | | 235 | 280 | 45 | | |
| | | 0.05 | 120 | 210 | 235 | 25 | 25 | 50 |
| | | | | 220 | 245 | 25 | | |
| | | 0.1 | | 220 | 245 | 25 | 32.5 | 43 |
| | | | | 235 | 275 | 40 | | |
| | | 0.05 | 180 | 195 | 245 | 50 | 47.5 | 5 |
| | | | | 230 | 275 | 45 | | |
| | | 0.1 | | 200 | 250 | 50 | 50 | 13 |
| | | | | 230 | 280 | 50 | | |
| | | 0.05 | 240 | 195 | 245 | 55 | 52.5 | −5 |
| | | | | 225 | 275 | 50 | | |
| | | | | 225 | 275 | 50 | | |
| | | | | 210 | 250 | 40 | 45 | 22 |
| | | | | 235 | 285 | 50 | | |
| | | 0.05 | 300 | 195 | 245 | 50 | 50 | 0 |
| | | | | 210 | 260 | 50 | | |
| | | 0.1 | | 205 | 245 | 40 | 55 | 4 |
| | | | | 215 | 285 | 70 | | |
| SPONTANEOUSLY HYPERTENSIVE RATS n = 2 Body weight(s): 370,360 grams | | | | | | | | |
| CONTROL | | 0.05 | 0 | 255 | 285 | 30 | 25 | |
| | | | | 235 | 255 | 20 | | |
| | | 0.1 | | 235 | 280 | 45 | 34.5 | |
| | | | | 233 | 257 | 24 | | |
| 38 | 3 p.o. | 0.05 | 30 | 227 | 237 | 10 | 7.5 | 70 |
| | | | | 235 | 240 | 5 | | |
| | | 0.1 | | 225 | 250 | 25 | 15 | 57 |
| | | | | 235 | 240 | 5 | | |
| | | 0.05 | 60 | 230 | 240 | 10 | 12.5 | 50 |
| | | | | 230 | 245 | 15 | | |
| | | 0.1 | | 215 | 255 | 40 | 27.5 | 20 |
| | | | | 225 | 240 | 15 | | |
| | | 0.05 | 90 | 225 | 235 | 10 | 13.5 | 46 |
| | | | | 233 | 250 | 17 | | |
| | | 0.1 | | 215 | 245 | 30 | 23.5 | 32 |
| | | | | 235 | 252 | 17 | | |
| | | 0.05 | 120 | 225 | 230 | 5 | 7.5 | 70 |
| | | | | 235 | 245 | 10 | | |
| | | 0.1 | | 220 | 240 | 20 | 16.5 | 52 |
| | | | | 240 | 253 | 13 | | |
| | | 0.05 | 180 | 230 | 235 | 5 | 7.5 | 70 |
| | | | | 240 | 250 | 10 | | |
| | | 0.1 | | 225 | 255 | 30 | 25 | 28 |
| | | | | 235 | 255 | 20 | | |
| | | 0.05 | 240 | 230 | 240 | 10 | 15 | 40 |
| | | | | 240 | 260 | 20 | | |
| | | 0.1 | | 225 | 260 | 35 | 29 | 16 |
| | | | | 237 | 260 | 23 | | |
| SPONTANEOUSLY HYPERTENSIVE RATS n = 2 Body weight(s): 330,340 grams | | | | | | | | |
| CONTROL | | 0.05 | 0 | 200 | 245 | 45 | 40 | |
| | | | | 220 | 255 | 35 | | |
| | | | | 195 | 250 | 55 | 45 | |

TABLE II-continued

| | | ANGIOTENSIN II (AII) VASOPRESSOR RESPONSE | | | | | | |
|---|---|---|---|---|---|---|---|---|
| Ex. No. | Dose (mg/kg) | AII Dose mcg/kg IV | Min Post Dose | Control Before AII | Response After AII | Change | Average Change | % Inhibition |
| | | | | 220 | 255 | 35 | | |
| 42 | 3 p.o. | 0.05 | 30 | 210 | 240 | 30 | 32.5 | 19 |
| | | | | 210 | 245 | 35 | | |
| | | 0.1 | | 195 | 240 | 45 | 35 | 22 |
| | | | | 220 | 250 | 30 | | |
| | | 0.05 | 60 | 195 | 230 | 35 | 32.5 | 19 |
| | | | | 220 | 250 | 30 | | |
| | | 0.1 | | 190 | 235 | 45 | 35 | 22 |
| | | | | 225 | 250 | 25 | | |
| | | 0.05 | 90 | 200 | 215 | 15 | 20 | 50 |
| | | | | 215 | 240 | 25 | | |
| | | 0.1 | | 195 | 235 | 40 | 39 | 13 |
| | | | | 210 | 248 | 38 | | |
| | | 0.05 | 120 | 185 | 210 | 25 | 32.5 | 19 |
| | | | | 200 | 240 | 40 | | |
| | | 0.1 | | 180 | 220 | 40 | 40 | 11 |
| | | | | 205 | 245 | 40 | | |
| | | 0.05 | 180 | 205 | 245 | 40 | 41 | −2 |
| | | | | 200 | 242 | 42 | | |
| | | 0.1 | | 205 | 250 | 45 | 45 | 0 |
| | | | | 215 | 260 | 45 | | |
| SPONTANEOUSLY HYPERTENSIVE RATS n = 2 Body weight(s): 380,350 grams | | | | | | | | |
| CONTROL | | 0.05 | 0 | 230 | 260 | 30 | 35 | |
| | | | | 220 | 260 | 40 | | |
| | | 0.1 | | 235 | 260 | 25 | 42.5 | |
| | | | | 215 | 275 | 60 | | |
| 42 | 10 i.v. | 0.05 | 30 | 220 | 220 | 0 | 0 | 100 |
| | | | | 235 | 235 | 0 | | |
| | | 0.1 | | 210 | 210 | 0 | 0 | 100 |
| | | | | 230 | 230 | 0 | | |
| | | 0.05 | 60 | 210 | 210 | 0 | 5 | 86 |
| | | | | 215 | 225 | 10 | | |
| | | 0.1 | | 200 | 200 | 0 | 7.5 | 82 |
| | | | | 210 | 225 | 15 | | |
| | | 0.05 | 90 | 210 | 210 | 0 | 2.5 | 93 |
| | | | | 220 | 225 | 5 | | |
| | | 0.1 | | 200 | 215 | 15 | 10 | 76 |
| | | | | 215 | 220 | 5 | | |
| | | 0.05 | 120 | 190 | 190 | 0 | 2.5 | 93 |
| | | | | 210 | 215 | 5 | | |
| | | 0.1 | | 180 | 195 | 15 | 15 | 65 |
| | | | | 200 | 215 | 15 | | |
| | | 0.05 | 180 | 185 | 185 | 0 | 12.5 | 64 |
| | | | | 215 | 240 | 25 | | |
| | | 0.1 | | 180 | 180 | 0 | 17.5 | 59 |
| | | | | 215 | 250 | 35 | | |
| | | 0.05 | 240 | 175 | 190 | 15 | 20 | 43 |
| | | | | 200 | 225 | 25 | | |
| | | 0.1 | | 180 | 190 | 10 | 15 | 65 |
| | | | | 210 | 230 | 20 | | |
| | | 0.05 | 300 | 165 | 175 | 10 | 20 | 43 |
| | | | | 200 | 230 | 30 | | |
| | | 0.1 | | 175 | 180 | 5 | 22.5 | 47 |
| | | | | 200 | 240 | 40 | | |
| SPONTANEOUSLY HYPERTENSIVE RATS n = 2 Body weight(s): 330,335 grams | | | | | | | | |
| CONTROL | | 0.05 | 0 | 265 | 295 | 30 | 32.5 | |
| | | | | 200 | 235 | 35 | | |
| | | 0.1 | | 270 | 297 | 27 | 31 | |
| | | | | 205 | 240 | 35 | | |
| 43 | 10 i.v. | 0.05 | 30 | 255 | 255 | 0 | 0 | 100 |
| | | | | 200 | 200 | 0 | | |
| | | 0.1 | | 250 | 255 | 5 | 2.5 | 92 |
| | | | | 200 | 200 | 0 | | |
| | | 0.05 | 60 | 250 | 255 | 5 | 7.5 | 77 |
| | | | | 185 | 195 | 10 | | |
| | | 0.1 | | 255 | 260 | 5 | 5 | 84 |
| | | | | 190 | 195 | 5 | | |
| | | 0.05 | 90 | 255 | 265 | 10 | 10 | 69 |
| | | | | 180 | 190 | 10 | | |
| | | 0.1 | | 255 | 260 | 5 | 5 | 84 |
| | | | | 185 | 190 | 5 | | |
| | | 0.05 | 120 | 245 | 255 | 10 | 10 | 69 |
| | | | | 180 | 190 | 10 | | |
| | | 0.1 | | 250 | 265 | 15 | 10 | 68 |
| | | | | 185 | 190 | 5 | | |
| | | 0.05 | 180 | 250 | 260 | 10 | 13.5 | 58 |
| | | | | 190 | 207 | 17 | | |
| | | 0.1 | | 255 | 275 | 20 | 17.5 | 44 |
| | | | | 185 | 200 | 15 | | |

TABLE II-continued

ANGIOTENSIN II (AII) VASOPRESSOR RESPONSE

| Ex. No. | Dose (mg/kg) | AII Dose mcg/kg IV | Min Post Dose | Control Before AII | Response After AII | Change | Average Change | % Inhibition |
|---|---|---|---|---|---|---|---|---|
| | | 0.05 | 240 | 245 | 290 | 45 | 32.5 | 0 |
| | | | | 190 | 210 | 20 | | |
| | | 0.1 | | 285 | 290 | 5 | 13.5 | 56 |
| | | | | 185 | 207 | 22 | | |
| | | 0.05 | 300 | 245 | 285 | 40 | 30 | 8 |
| | | | | 190 | 210 | 20 | | |
| | | 0.1 | | 260 | 290 | 30 | 25 | 19 |
| | | | | 195 | 215 | 20 | | |

SPONTANEOUSLY HYPERTENSIVE RATS n = 2 Body weight(s): 360,350 grams

| Ex. No. | Dose (mg/kg) | AII Dose mcg/kg IV | Min Post Dose | Control Before AII | Response After AII | Change | Average Change | % Inhibition |
|---|---|---|---|---|---|---|---|---|
| CONTROL | | 0.05 | 0 | 190 | 230 | 40 | 42.5 | |
| | | | | 195 | 240 | 45 | | |
| | | 0.1 | | 195 | 235 | 40 | 40 | |
| | | | | 200 | 240 | 40 | | |
| 43 | 3 p.o. | 0.05 | 30 | 190 | 225 | 35 | 32.5 | 24 |
| | | | | 190 | 220 | 30 | | |
| | | 0.1 | | 195 | 230 | 35 | 32.5 | 19 |
| | | | | 195 | 225 | 30 | | |
| | | 0.05 | 60 | 205 | 235 | 30 | 22.5 | 47 |
| | | | | 190 | 205 | 15 | | |
| | | 0.1 | | 200 | 240 | 40 | 32.5 | 19 |
| | | | | 190 | 215 | 25 | | |
| | | 0.05 | 90 | 205 | 225 | 20 | 20 | 53 |
| | | | | 190 | 210 | 20 | | |
| | | 0.1 | | 215 | 225 | 10 | 17.5 | 56 |
| | | | | 195 | 220 | 25 | | |
| | | 0.05 | 120 | 200 | 220 | 20 | 20 | 53 |
| | | | | 195 | 215 | 20 | | |
| | | 0.1 | | 195 | 220 | 25 | 22.5 | 44 |
| | | | | 195 | 215 | 20 | | |
| | | 0.05 | 180 | 190 | 205 | 15 | 17.5 | 59 |
| | | | | 190 | 210 | 20 | | |
| | | 0.1 | | 190 | 230 | 40 | 37.5 | 6 |
| | | | | 190 | 225 | 35 | | |
| | | 0.05 | 240 | 190 | 210 | 15 | 27.5 | 35 |
| | | | | 190 | 230 | 40 | | |
| | | 0.1 | | 185 | 215 | 30 | 35 | 13 |
| | | | | 190 | 230 | 40 | | |
| | | 0.05 | 300 | 185 | 225 | 40 | 40 | 6 |
| | | | | 190 | 230 | 40 | | |
| | | 0.1 | | 188 | 237 | 49 | 37 | 8 |
| | | | | 190 | 215 | 25 | | |

SPONTANEOUSLY HYPERTENSIVE RATS n = 2 Body weight(s): 350,350 grams

| Ex. No. | Dose (mg/kg) | AII Dose mcg/kg IV | Min Post Dose | Control Before AII | Response After AII | Change | Average Change | % Inhibition |
|---|---|---|---|---|---|---|---|---|
| CONTROL | | 0.05 | 0 | 200 | 235 | 35 | 40 | |
| | | | | 235 | 280 | 45 | | |
| | | 0.1 | | 200 | 240 | 40 | 42.5 | |
| | | | | 235 | 280 | 45 | | |
| 47 | 3 i.v. | 0.05 | 30 | 200 | 210 | 10 | 10 | 75 |
| | | | | 230 | 240 | 10 | | |
| | | 0.1 | | 190 | 198 | 8 | 11.5 | 73 |
| | | | | 220 | 235 | 15 | | |
| | | 0.05 | 60 | 195 | 195 | 0 | 10 | 75 |
| | | | | 210 | 230 | 20 | | |
| | | 0.1 | | 190 | 205 | 15 | 15 | 65 |
| | | | | 225 | 240 | 15 | | |
| | | 0.05 | 90 | 190 | 195 | 5 | 15 | 63 |
| | | | | 220 | 245 | 25 | | |
| | | 0.1 | | 200 | 205 | 5 | 10 | 76 |
| | | | | 225 | 240 | 15 | | |
| | | 0.05 | 120 | 190 | 195 | 5 | 12.5 | 69 |
| | | | | 215 | 235 | 20 | | |
| | | 0.1 | | 195 | 200 | 5 | 7.5 | 82 |
| | | | | 225 | 235 | 0 | | |
| | | 0.05 | 180 | 193 | 198 | 5 | 10 | 75 |
| | | | | 215 | 230 | 15 | | |
| | | 0.1 | | 185 | 200 | 15 | 17.5 | 59 |
| | | | | 210 | 230 | 20 | | |
| | | 0.05 | 240 | 190 | 205 | 15 | 25 | 38 |
| | | | | 215 | 250 | 35 | | |
| | | 0.1 | | 195 | 230 | 35 | 30 | 29 |
| | | | | 230 | 255 | 25 | | |
| | | 0.05 | 300 | 185 | 207 | 22 | 28.5 | 29 |
| | | | | 220 | 255 | 35 | | |
| | | 0.1 | | 200 | 230 | 30 | 35 | 18 |
| | | | | 235 | 275 | 40 | | |

SPONTANEOUSLY HYPERTENSIVE RATS n = 2 Body weight(s): 410,410 grams

| Ex. No. | Dose (mg/kg) | AII Dose mcg/kg IV | Min Post Dose | Control Before AII | Response After AII | Change | Average Change | % Inhibition |
|---|---|---|---|---|---|---|---|---|
| CONTROL | | 0.05 | 0 | 210 | 252 | 42 | 43.5 | |
| | | | | 215 | 260 | 45 | | |
| | | 0.1 | | 210 | 260 | 50 | 52.5 | |
| | | | | 210 | 265 | 55 | | |

TABLE II-continued

ANGIOTENSIN II (AII) VASOPRESSOR RESPONSE

| Ex. No. | Dose (mg/kg) | AII Dose mcg/kg IV | Min Post Dose | Control Before AII | Response After AII | Change | Average Change | % Inhibition |
|---|---|---|---|---|---|---|---|---|
| 48 | 3 i.v. | 0.05 | 30 | 210 | 212 | 2 | 3.5 | 92 |
| | | | | 200 | 205 | 5 | | |
| | | 0.1 | | 200 | 205 | 5 | 25 | 95 |
| | | | | 200 | 200 | 0 | | |
| | | 0.05 | 60 | 200 | 205 | 5 | 5 | 89 |
| | | | | 195 | 200 | 5 | | |
| | | 0.1 | | 205 | 205 | 0 | 0 | 100 |
| | | | | 200 | 200 | 0 | | |
| | | 0.05 | 90 | 195 | 205 | 10 | 7.5 | 83 |
| | | | | 195 | 200 | 5 | | |
| | | 0.1 | | 195 | 200 | 5 | 2.5 | 95 |
| | | | | 195 | 195 | 0 | | |
| | | 0.05 | 120 | 190 | 193 | 3 | 1.5 | 97 |
| | | | | 210 | 210 | 0 | | |
| | | 0.1 | | 190 | 197 | 7 | 8.5 | 84 |
| | | | | 215 | 225 | 10 | | |
| | | 0.05 | 180 | 190 | 197 | 7 | 13.5 | 69 |
| | | | | 200 | 220 | 20 | | |
| | | 0.1 | | 190 | 200 | 10 | 22.5 | 57 |
| | | | | 200 | 235 | 35 | | |
| | | 0.05 | 240 | 195 | 205 | 10 | 14 | 68 |
| | | | | 200 | 218 | 18 | | |
| | | 0.1 | | 195 | 220 | 25 | | 52 |
| | | | | 205 | 230 | 25 | | |
| | | 0.05 | 300 | 185 | 195 | 10 | 12.5 | 71 |
| | | | | 210 | 225 | 15 | | |
| | | 0.1 | | 185 | 205 | 20 | 22.5 | 57 |
| | | | | 205 | 230 | 25 | | |
| SPONTANEOUSLY HYPERTENSIVE RATS n = 2 Body weight(s): 400,400 grams | | | | | | | | |
| CONTROL | | 0.05 | 0 | 245 | 290 | 45 | 42.5 | |
| | | | | 210 | 250 | 40 | | |
| | | 0.1 | | 240 | 290 | 50 | 50 | |
| | | | | 210 | 260 | 50 | | |
| 52 | 10 i.v. | 0.05 | 30 | 225 | 240 | 15 | 12.5 | 71 |
| | | | | 205 | 215 | 10 | | |
| | | 0.1 | | 225 | 235 | 10 | 7.5 | 85 |
| | | | | 210 | 215 | 5 | | |
| | | 0.05 | 60 | 240 | 245 | 5 | 2.5 | 94 |
| | | | | 210 | 210 | 0 | | |
| | | 0.1 | | 240 | 250 | 10 | 5 | 90 |
| | | | | 210 | 210 | 0 | | |
| | | 0.05 | 90 | 225 | 240 | 15 | 10 | 76 |
| | | | | 220 | 225 | 5 | | |
| | | 0.1 | | 210 | 235 | 25 | 15 | 70 |
| | | | | 220 | 225 | 5 | | |
| | | 0.05 | 120 | 215 | 230 | 15 | 17.5 | 59 |
| | | | | 220 | 240 | 20 | | |
| | | 0.1 | | 210 | 225 | 15 | 10 | 80 |
| | | | | 225 | 230 | 5 | | |
| | | 0.05 | 180 | 210 | 245 | 35 | 22.5 | 47 |
| | | | | 220 | 230 | 10 | | |
| | | 0.1 | | 220 | 255 | 35 | 22.5 | 55 |
| | | | | 220 | 230 | 10 | | |
| | | 0.05 | 240 | 225 | 255 | 30 | 30 | 29 |
| | | | | 220 | 250 | 30 | | |
| | | 0.1 | | 225 | 260 | 35 | 27.5 | 45 |
| | | | | 230 | 250 | 20 | | |
| | | 0.05 | 300 | 225 | 260 | 35 | 22.5 | 47 |
| | | | | 225 | 235 | 10 | | |
| | | 0.1 | | 240 | 275 | 35 | 27.5 | 45 |
| | | | | 220 | 240 | 20 | | |
| SPONTANEOUSLY HYPERTENSIVE RATS n = 2 Body weight(s): 375,390 grams | | | | | | | | |
| CONTROL | | 0.05 | 0 | 240 | 285 | 45 | 47.5 | |
| | | | | 225 | 275 | 50 | | |
| | | 0.1 | | 220 | 263 | 43 | 51.5 | |
| | | | | 225 | 285 | 60 | | |
| 53 | 3 i.v. | 0.05 | 30 | 210 | 215 | 5 | 5 | 89 |
| | | | | 215 | 220 | 5 | | |
| | | 0.1 | | 210 | 220 | 10 | 12.5 | 76 |
| | | | | 215 | 230 | 15 | | |
| | | 0.05 | 60 | 220 | 225 | 5 | 5 | 89 |
| | | | | 220 | 225 | 5 | | |
| | | 0.1 | | 215 | 240 | 25 | 20 | 61 |
| | | | | 215 | 230 | 15 | | |
| | | 0.05 | 90 | 220 | 230 | 10 | 20 | 58 |
| | | | | 215 | 245 | 30 | | |
| | | 0.1 | | 225 | 235 | 10 | 12.5 | 76 |
| | | | | 225 | 240 | 15 | | |
| | | 0.05 | 120 | 210 | 240 | 30 | 20 | 58 |

TABLE II-continued

| Ex. No. | Dose (mg/kg) | AII Dose mcg/kg IV | Min Post Dose | Control Before AII | Response After AII | Change | Average Change | % Inhibition |
|---|---|---|---|---|---|---|---|---|
| | | | | 215 | 225 | 10 | | |
| | | 0.1 | | 215 | 245 | 30 | 20 | 61 |
| | | | | 210 | 220 | 10 | | |
| | | 0.05 | 180 | 210 | 245 | 35 | 30 | 37 |
| | | | | 215 | 240 | 25 | | |
| | | 0.1 | | 215 | 240 | 25 | 30 | 42 |
| | | | | 225 | 260 | 35 | | |
| | | 0.05 | 240 | 210 | 230 | 20 | 20 | 58 |
| | | | | 205 | 225 | 20 | | |
| | | 0.1 | | 210 | 242 | 32 | 29.5 | 43 |
| | | | | 215 | 242 | 27 | | |
| | | 0.05 | 300 | 205 | 230 | 25 | 22.5 | 53 |
| | | | | 205 | 225 | 20 | | |
| | | 0.1 | | 215 | 260 | 45 | 42.5 | 17 |
| | | | | 210 | 250 | 40 | | |

SPONTANEOUSLY HYPERTENSIVE RATS n = 2 Body weight(s): 390,390 grams

As can be seen from Table I, the compounds demonstrate excellent Angiotensin II Receptor Binding activity.

The enzyme renin acts on a blood plasma $\alpha_2$-globulin, angiotensinogen, to produce angiotensin I, which is then converted by angiotensin converting enzyme to AII. The substance AII is a powerful vasopressor agent which is implicated as a causative agent for producing high blood pressure in mammals. Therefore, compounds which inhibit the action of the hormone angiotensin II (AII) are useful in alleviating angiotensin induced hypertension.

The compounds may be employed as pharmaceutically acceptable salts. Pharmaceutically acceptable salts includes both the metallic (inorganic) salts and organic salts; a list of which is given in *Remington's Pharmaceutical Sciences*, 17th Edition, pg 1418 (1985). It is well known to one skilled in the art that an appropriate salt form is chosen based on physical and chemical stability, flowability, hygroscopicity and solubility. Preferred salts of this invention for the reasons cited above include potassium, sodium, calcium, magnesium and ammonium salts.

When the compounds are employed for the above utility, they may be combined with one or more pharmaceutically acceptable carriers, for example, solvents, diluents and the like, and may be administered orally in such forms as tablets, capsules, dispersible powders, granules, or suspensions containing, for example, from about 0.05 to 5% of suspending agent, syrups containing, for example, from about 10 to 50% of sugar, and elixirs containing, for example, from about 20 to 50% ethanol, and the like, or parenterally in the form of sterile injectable solutions or suspension containing from about 0.05 to 5% suspending agent in an isotonic medium. Such pharmaceutical preparations may contain, for example, from about 0.05 up to about 90% of the active ingredient in combination with the carrier, more usually between about 5% and 60% by weight.

The effective dosage of active ingredient employed may vary depending on the particular compound employed, the mode of administration and the severity of the condition being treated. However, in general, satisfactory results are obtained when the compounds of the invention are administered at a daily dosage of from about 0.5 to about 500 mg/kg of animal body weight, preferably given in divided doses two to four times a day, or in sustained release form. For most large mammals the total daily dosage is from about 1 to 100 mg, preferably from about 2 to 80 mg. Dosage forms suitable for internal use comprise from about 0.5 to 500 mg of the active compound in intimate admixture with a solid or liquid pharmaceutically acceptable carrier. This dosage regimen may be administered to provide the optimal therapeutic response. For example, several divided doses may be administered daily or the dose may be proportionally reduced as indicated by the exigencies of the therapeutic situation.

These active compounds may be administered orally as well as by intravenous, intramuscular, or subcutaneous routes. Solid carriers include starch, lactose, dicalcium phosphate, microcrystalline cellulose, sucrose and kaolin, while liquid carriers include sterile water, polyethylene glycols, non-ionic surfactants and edible oils such as corn, peanut and sesame oils, as are appropriate to the nature of the active ingredient and the particular form of administration desired. Adjuvants customarily employed in the preparation of pharmaceutical compositions may be advantageously included, such as flavoring agents, coloring agents, preserving agents, and antioxidants, for example, vitamin E, ascorbic acid, BHT and BHA.

The preferred pharmaceutical composition from the standpoint of ease of preparation and administration are solid compositions, particularly tablets and hard-filled or liquid-filled capsules. Oral administration of the compounds is preferred.

These active compounds may also be administered parenterally or intraperitoneally. Solutions or suspensions of these active compounds as a free base or pharmacologically acceptable salt can be prepared in water suitably mixed with a surfactant such as hydroxypropylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders of the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol

What is claimed is:

1. A quinazolinone compound having the formula:

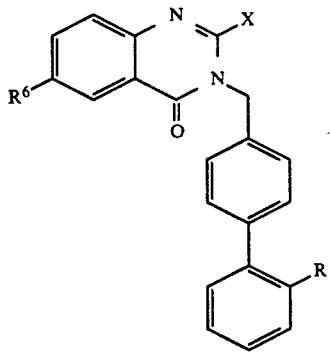

wherein:
R is

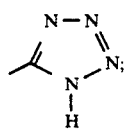

X is straight or branched alkyl of 3 to 5 carbon atoms;
$R^6$ is

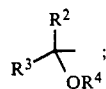

$R^2$ is H, or straight chain lower alkyl of 1 to 4 carbon atoms;
$R^3$ is

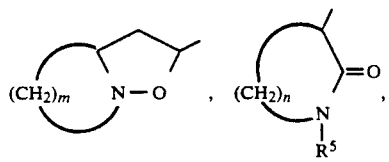

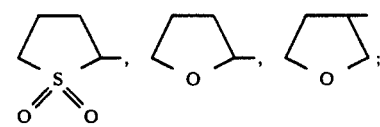

n is 2,S or 4;
m is 3 or 4;
$R^4$ is H, or straight chain lower alkyl of 1 to 4 carbon atoms;
$R^5$ is straight chain lower alkyl of 1 to 4 carbon atoms; and the pharmaceutically acceptable salts thereof.

2. The compound according to claim 1 wherein said salts are selected from potassium, sodium, calcium, magnesium or ammonium.

3. The compound according to claim 1 wherein X is a straight chain alkyl of 3 or 4 carbon atoms;
$R^3$ is

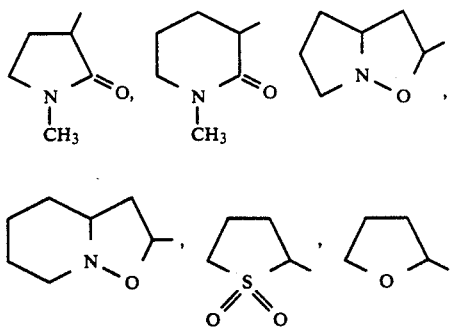

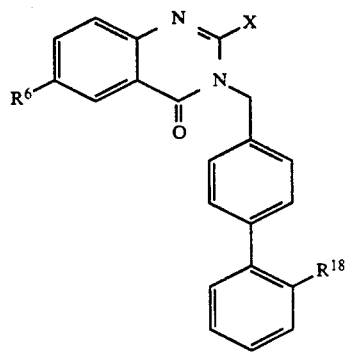

4. A quinazolinone compound having the formula:

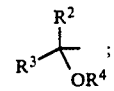

wherein:
X is straight or branched alkyl of 3 to 5 carbon atoms;
$R^6$ is

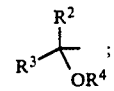

$R^2$ is H, or straight chain lower alkyl of 1 to 4 carbon atoms;
$R^3$ is

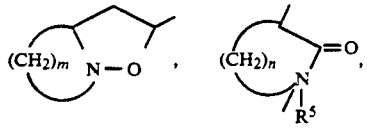

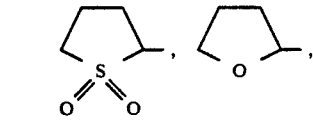

n is 2, 3 or 4;
m is 3 or 4;
$R^4$ is H, or straight chain lower alkyl of 1 to 4 carbon atoms;
$R^5$ is straight chain lower alkyl of 1 to 4 carbon atoms;

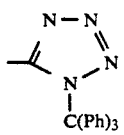

5. The compound according to claim 4 wherein X is a straight chain alkyl of 3 to 4 carbon atoms; R³ is

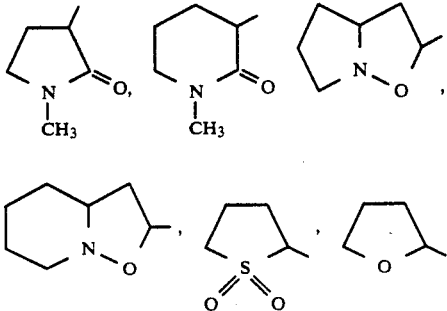

6. A quinazolinone compound having the formula:

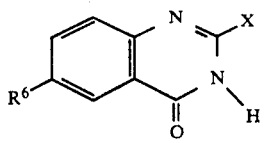

wherein
X is straight or branched alkyl of 3 to 5 carbon atoms;
R⁶ is

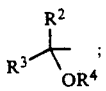

R² is H or straight chain lower alkyl of 1 to 4 carbon atoms;
R³ is

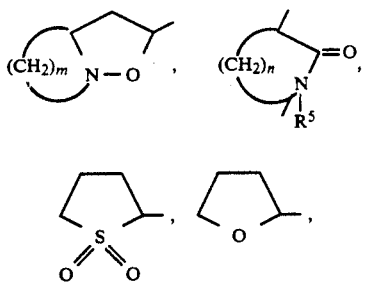

n is 2, 3 or 4;
m is 3 or 4;
R⁴ is H, or straight chain lower alkyl of 1 to 4 carbon atoms; R⁵ is straight chain lower alkyl of 1 to 4 carbon atoms.

7. The compound according to claim 6, wherein X is a straight chain alkyl of 3 or 4 carbon atoms; R³ is

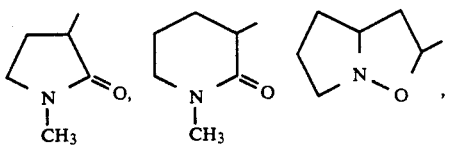

8. The compound according to claim 1, 2-(butyl-6-[hydroxy(tetrahydro-2-thienyl)methyl]-3-[[2'-(1H-tetrazol-5-yl)[1,1'-biphenyl]-4-yl]methyl]-4(3H)-quinazolinone S,S-dioxide.

9. The compound according to claim 1, 2-butyl-6-[methoxy(tetrahydro-2-furanyl)methyl]-3-[[2'-(1H-tetrazol-5-yl)[1,1'-biphenyl]-4-yl]-methyl]-4(3H)-quinazolinone.

10. The compound according to claim 1, 2-butyl-6-[hydroxy(tetrahydro-2-furanyl)methyl]-3-[[2'-(1H-tetrazol-5-yl)[1,1'-biphenyl]-4-yl]-methyl]-4(3H)-quinazolinone.

11. The compound according to claim, 1, 2-butyl-6-[hydroxy(1-methyl-2-oxo-3-pyrrolidinyl)methyl]-3-[[2'-(1H-tetrazol-5yl)[1,1'-biphenyl]-4-yl]methyl]-4(3H) quinazolinone.

12. The compound according to claim 1, 2-butyl-6-[hydroxy(1-methyl-2-oxo-3-piperidinyl)methyl]-3-[[2'-(1H-tetrazol-5-yl)[1,1'-biphenyl]-4-yl]methyl]-4(3H)-quinazolinone.

13. The compound according to claim 1, 2-butyl-6-[1-hydroxy-1-(1-methyl-2-oxo-3-pyrrolidinyl) ethyl]-3-[[2'[1H-(tetrazol-5-yl)-[1,1'-biphenyl]-4-yl]methyl-4(3H-quinazolinone.

14. The compound according to claim 1, 2-butyl-6-[1-hydroxy-1-(1-methyl-2-oxo-3-pyrrolidinyl) ethyl]-3-[[2'[1H-(tetrazol-5-yl)-[1,1'-biphenyl]-4-yl]methyl-4(3H)-quinazolinone, erythro isomer.

15. The compound according to claim 1, 2-butyl-6-[1-hydroxy-1-(1-methyl-2-oxo-3-pyrrolidinyl) -ethyl]-3-[[2'[1H-(tetrazol-5-yl)-[1,1'-biphenyl]-4-yl]-methyl-4(3H)-quinazolinone, threo isomer.

16. The compound according to claim 1, 2-butyl-6-[1-hydroxy-1-(1-methyl-2-oxo-3-pyrrolidinyl) -ethyl]-3-[[2',[1H-(tetrazol-5-yl)-[1,1'-biphenyl]-4-yl]-methyl-4(3H)-quinazolinone, sodium salt.

17. The compound according to claim 1, 2-butyl-6-[1-hydroxy-1-(1-methyl-2-oxo-3-pyrrolidinyl) -ethyl]-3-2'[1H-(tetrazol-5-yl)-[1,1'-biphenyl]-4-yl]-methyl-4(3H)-quinazolinone, erythro isomer, sodium salt.

18. The compound according to claim 1, 2-butyl-6-[1-hydroxy-1-(1-methyl-2-oxo-3-pyrrolidinyl) -ethyl]-3-[[2'[1H-(tetrazol-5-yl)-[1,1,-biphenyl]-4-yl]-methyl-4(3H)-quinazolinone, threo isomer, sodium salt.

19. The compound according to claim 1, 2-butyl-6-[methoxy(1-methyl-2-oxo-3-piperidinyl)methyl]-3-[[2'-(1H-tetrazol-5-yl)[1,1'-biphenyl]-4-yl]methyl]-4(3H)quinazoline.

20. The compound according to claim 4, 2-butyl-6-[hydroxy(tetrahydro-2-thienyl)methyl]-3-[[2'-[1-(triphenylmethyl)-1H-tetrazol-5-yl][1,1'-biphenyl]-4-yl]methyl]-3-quinazolinone S,S-dioxide.

21. The compound according to claim 4, 2-butyl-6-(2-furanylhydroxymethyl)-3-[[2'-[1-(triphenyl-methyl)-1H-tetrazol-5-yl][1,1'biphenyl]-4-yl]methyl-4(3H)-quinazolinone.

22. The compound according to claim 4, 2-butyl-6-(2-furanylmethoxymethyl)-3-[[2'-[1-(triphenyl methyl)-1H-tetrazol-5-yl][1,1'-biphenyl]-4-yl]methyl-4(3H)-quinazolinone.

23. The compound according to claim 4, 2-butyl-6-[methoxy(tetrahydro-2-furanyl)methyl]-3-[[2'-[1-(triphenylmethyl)-1H-tetrazol-5yl][1,1'-biphenyl]-4-yl]methyl]-4(3H) quinazolinone.

24. The compound according to claim 4, 2-butyl-6-[hydroxy(tetrahydro-2-furanyl)methyl]-3-[[2'-[1-(triphenylmethyl)-1H-tetrazol-5-yl][1,1'-biphenyl]-4-yl]methyl-4(3H-quinazolinone.

25. The compound according to claim 4, 2-butyl-6-[hydroxy(1-methyl-2-oxo-3-pyrrolidinyl) methyl-3-[[2'-[1-(triphenylmethyl)-1H-tetrazol-5-yl]-[1,1'-biphenyl]-4-yl]methyl]-4(3H-quinazolinone.

26. The compound according to claim 4, 2-butyl-6-[hydroxy(1-methyl-2-oxo-3-piperidinyl)methyl]-3-[[2'-[1-(triphenylmethyl )-1H-tetrazol-5-yl]-[1,1'-biphenyl]-4-yl]methyl-4(3H)-quinazolinone.

27. The compound according to claim 4, 2-butyl-6-[methoxy(1-methyl-2-oxo-3-piperidinyl)methyl]-3-[[2'-[1-(triphenylmethyl)-1H-tetrazol-5-yl][1,1'-biphenyl]-4-yl]methyl]-4(3H)quinazolinone.

28. The compound according to claim 4, 2-butyl-6-[methoxy(1-methyl-2-oxo-3-piperidinyl)methyl]-3-[[2'[1-triphenylmethyl)-1H-tetrazol-5-yl]-[1,1'-biphenyl]-4-yl]methyl]-4(3H)-quinazolinone.

29. The compound according to claim 6, 2-butyl-6-[hydroxy(tetrahydro-2-thienyl)methyl]-4(1H)-quinazolinone S,S-dioxide.

30. The compound according to claim 6, 2-butyl-6-(2-furanylhydroxymethyl)-4(1H)-quinazolinone.

31. The compound according to claim 6, 2-butyl-6-[hydroxy(tetrahydro-2-furanyl)methyl]-4(1H)-quinazolinone.

32. The compound according to claim 6, 2-butyl-6-[hydroxy(tetrahydro-2-furanyl)methyl]-4(1H)-quinazolinone.

33. The compound according to claim 6, 2-butyl-6-[hydroxy(1-methyl-2-oxo-3-pyrrolidinyl)methyl]-4(1H)-quinazolinone.

34. The compound according to claim 6, 2-butyl-6[hydroxy(1-methyl-2-oxo-3-pyrrolidinyl)methyl]-4(1H)-quinazolinone.

35. A pharmaceutical composition useful for treating angiotensin induced hypertension or congestive heart failure in a mammal comprising a suitable pharmaceutical carrier and an effective amount of a compound of claim 1.

36. A method of treating angiotensin induced hypertension in a mammal comprising administering a compound of claim 1 to said mammal an amount effective to lower angiotensin induced hypertension.

37. A method of treating congestive heart failure in a mammal comprising administering a compound of claim 1 to said mammal in an amount effective to treat congestive heart failure.

38. A method of antagonizing the effects of Angiotensin II in a mammal comprising administering a compound of claim 1 to said mammal in an amount effective to treat the effects of Angiotensin II.

* * * * *